United States Patent
Gorski et al.

(10) Patent No.: US 6,280,969 B1
(45) Date of Patent: *Aug. 28, 2001

(54) GROWTH ARREST HOMEOBOX GENE

(75) Inventors: David H. Gorski, Cleveland, OH (US); Kenneth Walsh, Concord, MA (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/078,465

(22) Filed: May 14, 1998

Related U.S. Application Data

(63) Continuation of application No. 08/203,532, filed on Feb. 24, 1994, now Pat. No. 5,856,121.

(51) Int. Cl.$^7$ .......................... C12N 15/12; C12N 15/63; C12N 1/21; C12N 5/10

(52) U.S. Cl. .................... 435/69.1; 435/69.4; 435/320.1; 435/252.3; 435/325; 530/399; 536/23.5

(58) Field of Search ..................... 536/23.5; 435/69.1, 435/69.4, 320.1, 252.3, 325; 530/399

(56) References Cited

U.S. PATENT DOCUMENTS 5,302,706   4/1994   Smith .................................. 536/23.1

OTHER PUBLICATIONS

"Molecular Cloning of a Homeobox Transcription Factor from Adult Aortic Smooth Muscle" by Patel, et al., *The Journal of Biological Chemistry*, vol. 267, No. 36, Dec. 25, 1992, pp. 26085–26090.

"Molecular Cloning of a Diverged Homeobox Gene that is Rapidly Down–Regulated During the $G_0/G_1$ Transition in Vascular Smooth Muscle Cells" by Gorski, et al., *Molecular and Cellular Biology*, vol. 13, No. 6, Jun. 1993, pp. 3722–3733.

"Homeobox Transcription Factor Regulation in the Cardiovascular System" by Gorski, et al., *TCM*, vol. 3, No. 5, 1993, pp. 184–190.

"Cloning and Sequence Analysis of Homeobox Transcription Factor cDNA's with an Inosine–Containing Probe" by Gorski, et al., *Short Technical Reports*, vol. 15, No. 5, 1994.

"The Growth Arrest–Specific Gene, gas 1, Is Involved in Growth Suppression" by Del Sal, et al., *International Centre for Genetic Engineering and Biotechnology*, Aug. 21, 1992, pp. 595–607.

"Cloning of Senescent Cell–Derived Inhibitors of DNA Synthesis Using an Expression Screen" by Noda, et al., *Experimental Cell Research*, 211, 1994, pp. 90–98.

"CHOP (GADD153) and its oncogenic variant, TLS–CHOP, have opposing effects on the induction of $G_1/S$ arrest" by Barone, et al., *Genes and Devlopment*, 8, 1994, pp. 453–464.

"Mox–1 and Mox–2 define a novel homeobox gene subfamily and are differentially expressed during early mesodermal petterning in mouse embryos" by Candia, et al., *Development*, 116, Aug. 28, 1992, pp. 1123–1136.

"Arterial Gene Transfer Using Pure DNA Applied Directly to a Hydrogel–Coated Anioplasty Balloon" by Riessen, et al., *Human Gene Therapy*, 4, 1993, pp. 749–758.

"Antisense c–myb oligonucleotides inhibit intimal arterial smooth muscle cell accumulation in vivo" by Simons, et al., *Nature*, vol. 359, Sep. 3, 1992, pp. 67–70.

"Site–Specific Gene Expression in Vivo by Direct Gene Transfer into the Arterial Wall" by Nabel, et al., *Reports*, Sep. 14, 1990, pp. 1285–1288.

"Low Level In Vivo Gene Transfer Into the Arterial Wall Through a Perforated Ballon Catheter" by Flugelman, et al., *Circulation*, vol. 85, No. 3, Mar. 1992, pp. 1110–1117.

"Single–step purification of polypeptides expressed in *Escherichia coli* as fusions with glutathione S–transferase" by Smith, et al., *Gene*, 67, 1988, pp. 31–40.

"Molecular Cloning and Localization of the Human Gax Gene to 7p21" by LePage, et al., *Genomics*, 24, 1994, pp. 535–540.

"Amino acid sequence of Mox–2 and comparsion to its Xenopus and rat homologs" by Candia, et al., *Nucleic Acids Research*, vol. 21, No. 21, 1993 p. 4982.

Exhibit A is the gene sequence for the rat Gax cDNA (2244 base pairs) submitted by Kenneth Walsh, released to the public Feb. 28, 1993.

Exhibit $B_1$ is a gene sequence for Mox–1 (2182 base pairs) (mistakenly designated "Mox–2") submitted by A.F. Candia to New GenBank and created on Sep. 25, 1992.

Exhibit $B_2$ is the same gene sequence as Exhibit $B_1$ except the former designation "Mox–2" has been corrected to read "Mox–1".

Exhibit C is the partial gene sequence for mouse Mos–2A submitted by A.F. Candia to GenBank and created on Oct. 5, 1992.

Exhibit D is the revision of Exhibit C to show the 1440 base pair mouse Mox–2 sequence on Mar. 6, 1993.

*Primary Examiner*—Rebecca E. Prouty
*Assistant Examiner*—Richard Hutson
(74) *Attorney, Agent, or Firm*—Calfee, Halter & Griswold LLP

(57) ABSTRACT

A novel growth arrest homeobox gene has been discovered and the nucleotide sequences have been determined in both the rat and the human. The expression of the novel homeobox gene inhibits vascular smooth muscle cell growth. The growth arrest homeobox gene hereinafter referred to as the "Gax gene" and its corresponding proteins are useful in the study of vascular smooth muscle cell proliferation and in the treatment of blood vessel diseases that result from excessive smooth muscle cell proliferation, particularly after balloon angioplasty.

20 Claims, 10 Drawing Sheets

FIG. 1A

```
                                                                                                    100
GTCAAGTGTTTATACGTGCAGGAGACTGGCCGCTCGGCTCAGGACTGGGATTAGCGGGCTCTGCTCAAACCCGCGGGCTTTTACATTAGGAGTGAGTGG
                                                                                                    199
GGGAGAGTCCTAGGATTCTAGTGAAAAGTGACACAGCGCTTGGTGGTGGACTTTGGGACTTGGACTTCTCTGTGAAGTCTTCTGCTTGGAAGCTGAGACTTGCATGCC ATG
                                                                                                      M   1

GAA CAC CCC CTC TTT GGC TGC CTG CGC AGC CCC CAC GCC ACA GCG CAA GGC TTG CAC CCC TTC TCG CAG TCT TCT    274
 E   H   P   L   F   G   C   L   R   S   P   H   A   T   A   Q   G   L   H   P   F   S   Q   S   S     26

CTG GCC CTC CAT GGA AGA TCT GAC CAC ATG TCC TAC CCC GAA CTC TCC ACA TCT TCC TCG TCT TGC ATA ATC GCG    349
 L   A   L   H   G   R   S   D   H   M   S   Y   P   E   L   S   T   S   S   S   S   C   I   I   A     51

GGA TAC CCC AAT GAG GAG GGC ATG TTT GCC CAG CAG CAT CAC AGG GGG CAC CAC CAC CAC CAC CAC CAC CAC CAT    424
 G   Y   P   N   E   E   G   M   F   A   S   Q   H   H   R   G   H   H   H   H   H   H   H   H   H     76

CAC CAC CAC CAG CAG CAG CAG CAG CAG CAG CTC CAA AGC AAC TGG CAC CTC CCG CAG ATG TCC TCC CCG CCA AGC    499
 H   H   H   Q   Q   Q   Q   Q   Q   Q   L   Q   S   N   W   H   L   P   Q   M   S   S   P   P   S    101

GCG GCC CGG CAC AGC CTT TGC CTG CAG CCT GAT CCA AGC ACC CCG GAG CTG GGA AGC CCT CCG GTC CTC            574
 A   A   R   H   S   L   C   L   Q   P   D   P   S   T   P   E   L   G   S   P   P   V   L            126

TGC TCC AAC TCT TCT AGC CTG GGC AGC AGT ACC CCG GCG GCC GCA CCA AGG GAT TAT GGC CGT CAA                649
 C   S   N   S   S   S   L   G   S   S   T   P   T   G   A   A   A   P   R   D   Y   G   R   Q        151

GCG CTG TCA CCC GCA GAA GTG GAG AAG AGA AGT GGC AGC AAA AGA AAA AGC GAC AGT TCA GAT TCC CAG GAA GGA    724
 A   L   S   P   A   E   V   E   K   R   S   G   S   K   R   K   S   D   S   S   D   S   Q   E   G    176

AAT TAC AAG TCA GAA GTG AAC AGC AAA CCT AGG AAG GAA AGA ACA GCT TTC ACC AAA GAG CAA ATC AGA GAA CTT    799
 N   Y   K   S   E   V   N   S   K   P   R   K   E   R   T   A   F   T   K   E   Q   I   R   E   L    201

GAG GCA GAG TTC GCC CAT CAT AAC TAT CTG ACC AGA CTG AGA AGA TAT GAG ATA GCG GTG AAC CTA GAC CTC ACT    874
 E   A   E   F   A   H   H   N   Y   L   T   R   L   R   R   Y   E   I   A   V   N   L   D   L   T    220
```

MATCH TO FIG. 1B

FIG. 1B

```
                MATCH TO FIG. 1A
GAA AGA CAG GTG AAA GTG TGG TTC CAG AAC AGG AGA ATG CGG AAC AGG GTC AAG GGG GGA CAA CAA GGA GCT    949
 E   R   Q   V   K   V   W   F   Q   N   R   R   M   R   N   R   V   K   G   G   Q   Q   G   A     251

GCA GCC CGA GAA AAG GAA CTG GTG AAT GTG AAA AAG GGA ACA CTT CTT CCA TCA GAG CTG TCA GGA ATT GGT GCA   1024
 A   A   R   E   K   E   L   V   N   V   K   K   G  (T)  L   L   P   S   E   L   S   G   I   G   A   276

GCC ACC CTC CAG CAG ACA GGG GAC TCA CTA GCA AAT GAC GAC AGT CGC GAT AGT GAC CAC AGC TCT GAG CAC GCA   1099
 A   T   L   Q   Q   T   G   D   S   L   A   N   D   D   S   R   D  (S)  D   H   S   S   E   H   A   301

CAC TTA TGA TACATACAGAGACCAGCTCCGTTCTCAGGAAGCACCATTGTGATGGCAAATCTCACCCAAACATCGTTACAGGCAGATGACTGTG    1196
 H   L  STOP                                                                                          303

GCAGTGTTGCTTAATATAATTAAACGCAGGCATCTCAAGTCTGTTTCTCATGATTGAATAGAAGGTTTACACTAAGTGCCTCTTATGAAGATGCTCCAC    1296

AGTGAAATTGGAGAAAGTGAACATATCTAAATACTTGTTCCTTATGACAGAGAGGGAGATGAATGTTGCTCACTGAAAATTAAATTG              1396

CTACCAAGAGCAAACTCGGTAAGACATTTTGACTCAAGTGTCTCCAGAGTGAAGATGTTATAGAAATGCTTTGAACATTCCAGTTGTACCAGGTCATGT   1496

GTGTGACACTGGGCAGGTATTTGCTTTTTGCTTGCACTGAAACTTAAACTGCTATCCAAGTTAACCCATGAAATAGTTTATCTTGAACAGCCACAGTGCCTG   1596

AAATCACCAAGTGGATATAAAATGAACTGAAATTCTGTATATATTACTCCTAAGTCATTTTCCGTCTTCACTAATTTTTAGCAAATGCATTCATATTAGC   1696

TGATGAAAATAGGCTTCCGTGGACAAATGCAGCCAGCTCTGTATTTTTGTCAGTCAGAGACATCAGTATGTGCTTACTGTGTT                   1796

CAAGTAGGAAATGCAGTAGAGTCTGATAGGACATATTCTGGTACCACAGACAAACAATCTCTGTTGCATTGACTATCAACTGCTGCAGATACAT        1896

TAGAGAACACACCTAGCCCCCCCTCCAGCTCCCTCCCTCCTGTTATCGCTCGAAGACATTAGGGTCATGGAAGTAGTTACCTGCCAAATGAGTCTGTGTGG   1996

CAGATGTCTGATTTGTATCTTTAAACTGTTAATGGTATGTGTCTGCTTCAGTTAACAGGGAAAAAGATTCTTCCTCATTGTTATGACAAACCCA        2096

AGTGCCAACAAAGCTAGTTCTTCAAGGGATAGATGAGAAACTGAATGTCTGACAAGTAGACTCAGCGAAATACATTATTTTCAGAGGCTGTGTATTC     2196

ATGCAGTACAAGTCCTTGTATTTGTAAAAAAAAAGTTAAATAAATG                                                         2244
```

FIG. 3

```
GTCTTCTACTGGAACCCGAAACTTGCATGCT ATG GAA CAC CCG CTC TTT GGC TGC CTG CGC AGC CCT CAC GCC ACG GCG CAA      83
                                 M   E   H   P   L   F   G   C   L   R   S   P   H   A   T   A   Q     17

GGC TTG CAC CCG TTC TCC CAA TCC TCT CTC GCC CTC CAT GGA AGA TCT GAC CAT ATG TCT TAC CCC GAG CTC TCT     158
 G   L   H   P   F   S   Q   S   S   L   A   L   H   G   R   S   D   H   M   S   Y   P   E   L   S     42

ACT TCT TCC TCA TCT TGC ATA ATC GCG GGA TAC CCC AAC GAA GAG GAC ATG TTT GCC AGC CAG CAT CAC AGG GGG     233
 T   S   S   S   S   C   I   I   A   G   Y   P   N   E   E   D   M   F   A   S   Q   H   H   R   G     67

CAC CAC CAC CAC CAC CAC CAC CAC CAC CAT CAG CAG CAG CAG CAG CAG CAG GCT CTG CAA ACC AAC TGG CAC CTC     300
 H   H   H   H   H   H   H   H   H   H   Q   Q   Q   Q   Q   Q   Q   A   L   Q   T   N   W   H   L     92

CCG CAG ATG TCT TCC CCA CCG AGT GCG GCT CGG AGT CAT CGG GCT CTC CTC GGC GAC TCT GGA GGG CCC CCA GAG     383
 P   Q   M   S   S   P   P   S   A   A   R   S   H   R   A   L   L   G   D   S   G   G   P   P   E    117

TTG GGG AGC AGC CCG CCC GTC CCG CTG TGC TCC AAC TCT TCC AGC TTG GGC TCC AGC ACC CCG ACT GGG GCC GCC TGC   450
 L   G   S   S   P   P   V   P   L   C   S   N   S   S   S   L   G   S   S   T   P   T   G   A   A   C  142

GCG CCG TCA GAC TCC GGG GAC TAC CGC CAG CGG CAG GAA TCA CCT GCG GAG CTG CGA AGC GGG AAG CGG AAG AGC     533
 A   P   S   D   S   G   D   Y   R   Q   R   Q   E   S   P   A   E   L   R   S   G   K   R   K   S    167

GAC AGC GAC TCC GAC CAG GAA GGC AAT TAC AAG TCA GAA GTC AAC AGC AAA CCC AGG AAA GAA AGG ACA GCA TTT     600
 D   S   D   S   D   Q   E   G   N   Y   K   S   E   V   N   S   K   P   R   K   E   R   T   A   F    192

ACC AAA GAG CAG ATC AGA GAA CTT GAA GCA GAA TTT GCC CAT CAT AAT TAT CTC ACC AGA CGA AGG CGA TAC GAG     683
 T   K   E   Q   I   R   E   L   E   A   E   F   A   H   H   N   Y   L   T   R   R   R   R   Y   E    217

ATA GCA GTG AAT CTG GAT CTC ACT GAA AGA CAG GTA AAA GTC TGG TTC CAA AAC CGG AGG ATG AAG TGG AAG AGG     758
 I   A   V   N   L   D   L   T   E   R   Q   V   K   V   W   F   Q   N   R   R   M   K   W   K   R    242

GTA AAG GGT GGA CAG CAA GGA GCT GCG GCT CGG CGG GAA AAG GAA CTG GTG AAT GTG AAG AAA GGA ACA CTT CTC CCA   833
 V   K   G   G   Q   Q   G   A   A   A   R   R   E   K   E   L   V   N   V   K   K   G   T   L   L   P  267

TCA GAG CTG TCG GGA ATT GGT GCA GCC ACC CTC CAG CAA ACA CAA GGG GAC TCT ATA GCA AAT GAA GAT CAC GAC     908
 S   E   L   S   G   I   G   A   A   T   L   Q   Q   T   Q   G   D   S   I   A   N   E   D   H   D    292

AGT GAC AGC AGC TCA GAG CAC AGC CAC CTC TGA                                                              941
 S   D   S   S   S   E   H   S   H   L   *                                                              302
```

GROWTH ARREST HOMEOBOX GENE

This application is a continuation of application Ser. No. 08/203,532, filed on Feb. 24, 1994 now issued as U.S. Pat. No. 5,856,121.

BACKGROUND OF THE INVENTION

The leading cause of death in the United States and in most developed countries, is atherosclerosis. Atherosclerosis is a disease affecting the large and medium size muscular arteries such as the coronary or carotid arteries and the large elastic arteries such as the aorta, iliac, and femoral arteries. This disease causes narrowing and calcification of arteries. The narrowing results from deposits of substances in the blood in combination with proliferating vascular smooth muscle cells.

The deposits known as atherosclerotic plaques are comprised of lipoproteins, mainly cholesterol, proliferating vascular smooth muscle cells and fibrous tissue, and extracellular matrix components, which are secreted by vascular smooth muscle cells. As the plaques grow, they narrow the lumen of the vessel decreasing arterial blood flow and weakening the effected arteries. The resulting complications potentially include a complete blockage of the lumen of the artery, with ischemia and necrosis of the organ supplied by the artery, ulceration and thrombus formation with associated embolism, calcification, and aneurysmal dilation. When atherosclerosis causes occlusion of the coronary arteries, it leads to myocardial disfunction, ischemia and infarction and often death. Indeed, 20–25% of deaths in the United States are attributable to atherosclerotic heart disease. Atherosclerosis also leads to lower extremity gangrene, strokes, mesenteric occlusion, ischemic encephalopathy, and renal failure, depending on the specific vasculature involved. Approximately 50% of all deaths in the United States can be attributed to atherosclerosis and its complications.

Present treatments for atherosclerosis include drugs and surgery, including ballon angioplasty. As a result of angioplasty, vascular smooth muscle cells de-differentiate and proliferate and leading to leading to reocclusion of the vessel. These de-differentiated vascular smooth muscle cells deposit collagen and other matrix substances, that contribute to the narrowing of vessel. Vascular cells secrete growth factors such as platelet derived growth factor, which induces both chemotaxis and proliferation of vascular smooth muscle cells.

Many of the present drug therapies treat a predisposing condition such as hyperlipidemia, hypertension, and hypercholesterolemia, in an attempt to slow or halt the progression of the disease. Other drug therapies are aimed at preventing platelet aggregation or the coagulation cascade. Unfortunately, the drug treatments do not reverse existing conditions.

Surgical treatments include coronary artery bypass grafting, balloon angioplasty, or vessel endarterectomy which, when successful, bypass or unblock occluded arteries thereby restoring blood flow through the artery. The surgical treatments do not halt or reverse the progression of the disease because they do not affect smooth muscle cell proliferation and secretion of extracellular matrix components.

The bypass surgeries, particularly the coronary bypass surgeries, are major, complicated surgeries which involve a significant degree of risk. The balloon angioplasty, while also a surgical procedure, is less risky. In balloon angioplasty, a catheter having a deflated balloon is inserted into an artery and positioned next to the plaque. The balloon is inflated thereby compressing the plaque against the arterial wall. As a result, the occlusion is decreased and increased blood flow is restored. However, the balloon angioplasty injures the arterial wall. As a result, the underlying vascular smooth muscle cells migrate to the intima, and synthesize and excrete extracellular matrix components eventually leading to the reocclusion of the vessel. Of the estimated 400,000 coronary artery balloon angioplasties performed each year in the United States, 40% fail due to reocclusion requiring a repeat procedure or coronary bypass surgery. Bypass surgeries also have a significant rate of failure due to internal hyperplasia, which involves excessive proliferation of vascular smooth muscle cells at the sites of vascular anastamoses.

Attempts have been made to prevent reocclusion of vessels after balloon angioplasties in experimental animals. One approach has been to treat rat carotid arteries with antisense oligonucleotides directed against the c-myb gene following balloon angioplasty de-endothelialization. In vascular smooth muscle cells expression of the c-myb gene is up-regulated during the G1 to S transition of the cell cycle, and the activation of c-myb expression is required for further cell cycle progression. The antisense oligonucleotides to c-myb blocked smooth muscle cell proliferation following balloon angioplasty. However, the antisense oligonucleotides are applied in a pleuronic gel to the adventitia, that is, the exterior, rather than the lumen side of the affected vessel. Exposing the the exterior of the vessel requires additional surgery with its attendant risks, and is therefore not desirable.

It would be desirable to have a nonsurgical treatment, used in conjunction with balloon angioplasties to reduce vascular smooth muscle cell proliferation.

SUMMARY OF THE INVENTION

A novel growth arrest homeobox gene has been discovered and the nucleotide sequences have been determined in both the rat and the human. The expression of the novel homeobox gene inhibits vascular smooth muscle cell growth. The growth arrest homeobox gene hereinafter referred to as the "Gax gene" and its corresponding proteins are useful in the study of vascular smooth muscle cell proliferation and in the treatment of blood vessel diseases that result from excessive smooth muscle cell proliferation, particularly after balloon angioplasty.

BRIEF DESCRIPTION OF THE DRAWINGS

The file of this patent contains at least one black and white photograph. Copies of this patent with black and white photographs will be provided by the Patent and Trademark Office upon request and payment of the necessary fee.

FIG. 1 is the nucleotide sequence SEQ ID NO: 1 of rat Gax gene with the predicted amino acid sequence SEQ ID NO: 2 listed below the nucleotide sequence. The homeobox is indicated by a box, and the CAX nucleotide repeat, where X is ether cytosine or guanine, is underlined. A polyadenylation signal is in boldface and italics. Putative consensus sites are indicated as follows: for phosphorylation by protein kinase C, circles; for cyclic AMP (cAMP)-dependent protein kinase, squares; for casein kinase II, diamonds; and for histone H1 kinase, triangles. Residues which could potentially be a target for either cAMP-dependent protein kinase or protein kinase C are both circled and boxed.

FIG. 3 is the nucleotide sequence SEQ ID NO: 3 of human Gax gene with the predicted amino acid sequence SEQ ID NO: 4 listed below the nucleotide sequence;

DETAILED DESCRIPTION OF THE INVENTION

Figure 2:
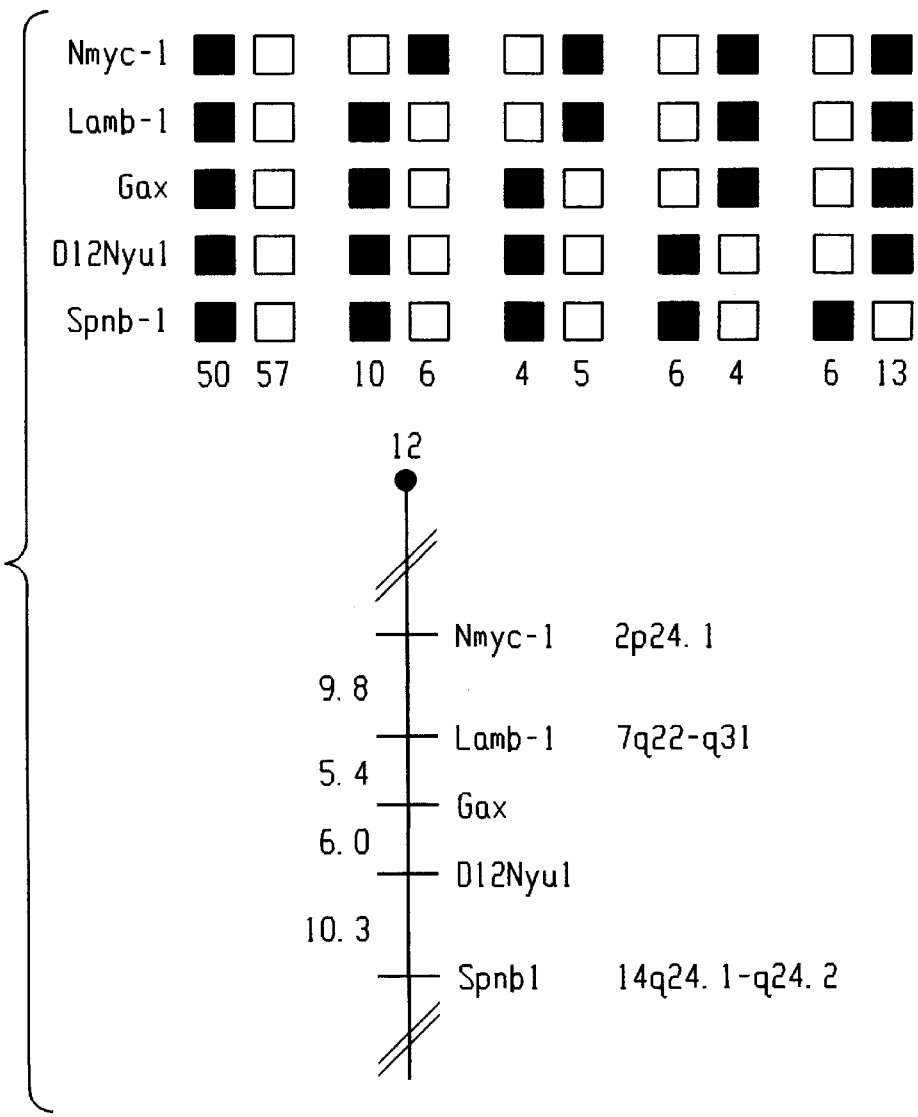
FIG. 2 is the map of mouse chromosome 12 showing the location of the Gax gene.

A novel gene, the Gax gene, has been discovered, the expression of which inhibits vascular smooth muscle cell growth. The Gax gene and the protein it encodes, referred to herein as the "Gax protein" are useful in the study of vascular smooth muscle cell proliferation and in inhibiting smooth muscle cell proliferation. The inhibition of vascular smooth muscle cell proliferation, particularly by genetic therapy, is also useful in the treatment of vascular diseases associated with excessive smooth muscle cell proliferation.

Nucleotide sequences, such as the Gax gene or portions therof, or mRNA are administered to the vascular cells, preferably during a balloon angioplasty procedure, to inhibit the proliferation of vascular smooth muscle cells. The nucleotide sequences are delivered, preferably to the interior of the vessel wall during balloon angioplasty procedure preferably by a perforated balloon catheter. Genes are transfered from vectors into vascular smooth muscle cells in vivo where the genes are expressed. Suitable vectors and procedures for the transfer of nucleotides are found in Nabel, E. G., et al. "Site-Specific Gene Expression in Vivo by Direct Gene Transfer into the Arterial Wall" (1990) *Science* Vol. 249, pp. 1285–1288, which is incorporated herein by reference. Specialized perforated balloon catheters which deliver nucleotide sequences to vessel walls employing viral and non-viral vectors are used for delivery of nucleotide sequences and a description of the catheter's structure and use may be found in Flugelman M. Y., et al. "Low Level In Vivo Gene Transfer Into the Arterial Wall Through a Perforated Balloon Catheter" *Circulation*, Vol. 85, No. 3, pp. 1110–1117 (March 1992) which is incorporated herein by reference.

Genetic therapy, preferably by the over expression of the Gax gene, restores the proliferating vascular smooth muscle cells to a more normal phenotype, thus preventing or reducing the smooth muscle proliferation that is associated with the formation of the atheromatous plaque and with internal arterial thickening following balloon angioplasty. In addition to preventing or reducing the reocclusion of the vessel, such genetic therapy decreases the risks associated with additional surgeries. Also, the Gax proteins or portions thereof, are administered to vascular cells preferably employing the perforated catheter, to inhibit the proliferation of vascular smooth muscle cells.

The molecular control of cellular proliferation is not well understood. A class of genes, known as Homeobox genes, encode a class of transcription factors which are important in embryogenesis, tissue specific gene expression and cell differentiation. The homeobox genes share a highly conserved 183 nucleotide sequence that is referred to as the "homeobox". The homeobox encodes a 61 amino acid helix-turn-helix motif that binds to adenine and thymine rich gene regulatory sequences with high affinity. Several vertebrate homeobox proteins have been shown to be transcription factors required for expression of lineage-specific genes. The tissue-specific transcription factors bind to DNA and repress or induce groups of subordinate genes. Many, but not all of these homeobox genes are located in one of four major clusters known as Hox clusters, designated Hox-1, Hox-2, Hox-3 and Hox-4. The Hox genes are expressed in the developing embryo, in distinct overlapping spatial patterns along the anterior-posterior axis which parallels the Hox gene order along the chromosome. Homeobox transcription factors control axial patterning, cell migration and differentiation in the developing embryo and are involved in the maintenance of tissue specific gene expression in adult organisms.

A new homebox gene has been discovered, isolated and sequenced in both the rat and human. This new gene is a growth arrest specific homeobox gene and is referred to herein as the "Gax gene". The expression of the Gax gene is restricted to the cardiovascular system, and in particular, to vascular smooth muscle cells where it functions as a negative regulator of cell proliferation.

Isolation of the Rat Gax cDNA

An adult rat aorta cDNA library in λ ZAP, from Stratagene, was screened with a 64-fold degenerate 29-mer oligonucleotide containing three inosine residues directed at the most highly conserved region of the antennapedia homeodomain (helix 3), with the following sequence SEQ ID NO: 5, where I represents inosine:

5'-AA(A/G)ATITGGTT(T/C)CA(A/G)AA(C/T)(A/C)GI (A/C) GIATGAA-3'.

Recombinant phage colonies in *Escherichia coli* were adsorbed in duplicate to nitrocellulose membranes and hybridized at 42° C. with this oligonucleotide end labeled with (γ-32P)ATP in a mixture containing 0.5 M sodium phosphate at pH 7.0, 7% sodium dodecyl sulfate, 1 mM EDTA, and 1% bovine serum albumin. The filters were washed with a final stringency of 0.5×SSC (1×SSC in 150 mM NaCl with 15 mM sodium citrate at pH 7.0)–0.1% sodium dodecyl sulfate at 42° C. and exposed to X-ray film. Thirteen positive signals were isolated and rescreened until the clones were plaque purified. The plasmids containing the clones in λ ZAP vector were then excised by the protocol recommended by the manufacturer and sequenced on both strands with sequenase version 2.0 from United States Biochemicals. From 500,000 plaques, 13 positive clones were isolated, 12 of which contained homeodomains. Nine of the isolated clones were derived from previously described homeobox genes: Hox-1.3, Hox-1.4, Hox-1.11, and rat homeobox R1b. However, three clones represented the cDNA designated herein as the "Gax" gene. Homology searches were performed via the GenBank and EMBL data bases, version 73, by using the BLAST algorithm (4).

Nucleotide Sequence of the Rat Gax Gene

The nucleotide sequence of the rat Gax gene SEQ ID NO: 1 is shown in FIG. 1. The cDNA encoding Gax is 2,244 base pairs in length, which corresponds to the size of the Gax transcript, that is the Gax mRNA, which is about 2.3 to 2.4 kb as determined by Northern blot analysis. The Gax cDNA has an open reading frame from nucleotide residues 197 to 1108 beginning with an in-frame methionine that conforms to the eukaryotic consensus sequence for the start of translation and is preceded by multiple stop codons in all three reading frames. The open reading frame of the CDNA predicts a 33.6-kDa protein SEQ ID NO: 2 containing 303 amino acids with a homeodomain from amino acid residues 185 to 245, as shown in FIG. 1. To confirm that this cDNA was capable, of producing a protein product, the Gax open reading frame was fused in frame to the pQE-9 *E. coil* expression vector, from Qiagen, Inc., Chatsworth, Calif. and expressed in bacteria according to Hochuli, E., et. al. (1988) "Genetic Approach to Facilitate Purification of Recombinant Proteins with. a Novel Metal Chelate Adsorbent" *Bio/Technology* Vol. 6, pp. 1321–1325. *E. coli* containing this plasmid expressed a new protein of about 30 to about 36 kDa as determined by sodium dodecyl sulfate-polyacrylamide gel electrophoresis, and extracts from these *E. coli* cells displayed a weak binding activity for the adenine and thymine rich, MHox-binding site in the creatine kinase M enhancer.

The cDNA encoding the rat Gax gene also contains a long 3'-untranslated region, from bases 1109 to 2244, with a polyadenylation signal at base 2237, as shown in FIG. 1. The region between amino acids 87 and 184 contains 23 serine amino acids out of 88 amino acids and 10 proline amino acids out of 88 amino acids and contains several consensus sequences for phosphorylation by protein kinases. Gax also possesses a structural feature which is also found in several transcription factors, including homeodomain proteins, known as the CAX or Opa transcribed repeat. The Opa transcribed repeat encodes a stretch of glutamines and histidines; in the rat Gax gene it encodes 18 residues, of which 12 are consecutive histidines. This motif is shared by other transcription factors, such as the zinc finger gene YY-1, as well as by several homeobox genes, including H2.0, HB24, ERA-1 (Hox-1.6), Dual bar, and Tes-1. The Gax protein may require post-translational modifications for full activity, modifications that bacterially produced proteins do not undergo. Since the Gax protein has multiple consensus sites for phosphorylation by protein kinases, it is possible that its activity is activated or otherwise modulated by phosphorylation at one or more of those sites.

The Gax Gene Maps to a Chromosome 12 of the Mouse Genome

Gax is located on chromosome 12 as shown in FIG. 2 of the mouse and is not a part of the Hox-1, Hox-2, Hox-3, or Hox-4 gene clusters, which are located on chromosomes 6, 11, 15, and 2, respectively, McGinnis, W., and R. Krumlauf, (1992) "Homeobox genes and Axial Patterning" *Cell*, Vol. 68, pp. 283–302. Also Gax does not cosegregate with any other homeobox genes previously mapped in the interspecific backcross. A comparison was done of the interspecific map of chromosome 12 with a composite mouse linkage map that reports the map location of many uncloned mouse mutations using GBASE, a computerized data base maintained at The Jackson Laboratory, Bar Harbor, Me. The Gax gene mapped in a region of the composite map that lacks mouse mutations with a phenotype that might be expected for an alteration in this locus.

The mouse chromosomal location of the Gax was determined by interspecific backcross analysis using progeny generated by mating (C57BL/6J×*Mus spretus*) $F_1$ females and C57BL/6J males. The C57BL/6J and *M. spretus* DNAs were digested with several enzymes and analyzed by Southern blot hybridization for informative restriction fragment length polymorphisms with a rat cDNA Gax probe. The probe, a 1,155-bp rat cDNA clone, was labeled with ($\alpha$-$^{32}$P) dCTP by using a random prime labeling kit from Amersham and washing was done with a final stringency of 0.2×SSCP (34)–0.1% sodium dodecyl sulfate, 65° C. A major fragment of 4.2 kb was detected in HincII-digested C57BL/6J DNA, and major fragments of 3.6 and 2.7 kb were detected in HincII-digested *M. spretus* DNA. The 3.6-kb and 2.7-kb *M. spretus* HincII restriction fragment length polymorphisms were used to monitor the segregation of the Gax locus in backcross mice. Recombination distances were calculated by using the computer program SPRETUS MADNESS. Gene order was determined by minimizing the number of recombination events required to explain the allele distribution patterns.

The mapping results indicated that the mouse Gax gene is located in the proximal region of mouse chromosome 12 linked to neuroblastoma myc-related oncogene 1 (Nmyc-1), the laminin B1 subunit gene (Lamb-1), a DNA segment, chromosome 12, the Nyu 1 gene (D12Nyu1), and the β-spectrin gene (Spnb-1). The ratios of the total number of mice exhibiting recombinant chromosomes to the total number of mice analyzed for each pair of loci and the most likely gene order are as follows: centromere-Nmyc-1-19/193-Lamb-1-9/166-Gax-10/166-D12Nyul-19/185-Spnb-1. The recombination frequencies, expressed as genetic distances in centimorgans ± the standard error, are as follows: Nmyc-1-9.8±2.2-Lamb-1-5.4±1.8-Gax-6.0±1.9-D12Nyul-10.3±2.2-Spnb-1.

Gax Gene Expression in Rat Tissue

It has been discovered that the Gax transcript is largely confined to the cardiovascular system, including the descending thoracic aorta, where it is expressed at higher levels than in other tissues, and the heart. Gax gene expression was also detected in the adult lung and kidney where it is found in mesangial cells. No Gax gene expression was detected in the brain, liver, skeletal muscle, spleen, stomach, or testes, nor was expression detected in the intestine or pancreas. In contrast, the Gax gene was more widely expressed in the developing embryo, with the transcript detectable in the developing cardiovascular system, multiple mesodermal tissues, and some ectodermal tissues.

The 2.3-kb to 2.4-kb Gax RNA transcript was detected in smooth muscle cells cultured from adult rat aorta, consistent with the in situ hybridization findings and the fact that Gax was originally isolated from a vascular smooth muscle library. The Gax transcript was also detected in rat vascular smooth muscle cells transformed by simian virus 40. However, no Gax gene expression was detected in either of two cell lines derived from embryonic rat aortic smooth muscle, A7r5 and A10. The Gax transcript was also not detected in NIH 3T3 fibroblasts, or human foreskin fibroblasts. The Gax transcript was not detected in the skeletal muscle cell line C2C12. A relatively high level of Gax gene expression was detected in cultured rat mesangial cells. Mesangial cells share many similarities to vascular smooth muscle cells, both structurally and functionally, and proliferate abnormally in renal diseases such as glomerulonephritis and glomerulosclerosis.

Isolation of the Human Gax cDNA

The nucleotide sequence SEQ ID NO: 3 of the human Gax gene coding sequence is shown in FIG. 3. Approximately $1 \times 10^6$ plaques from a human genomic library in λFixII available from Stratagene were screened by conventional methods with a random primed EcoRI/BstXI fragment encompassing nucleotides 485–1151 of the rat Gax cDNA. Two clones contained the second exon of human Gax gene, having 182 base pairs. Using this coding information, the rest of the coding region was cloned by polymerase chain reaction methods.

Reverse transcriptase and polymerase chain reaction techniques were used to clone the 3' end of the human cDNA. The template was whole human RNA isolated from human internal mammary artery isolated by TRI reagent from Molecular Research Center, Inc. The following reagent concentrations were used in the reverse transcriptase reaction: 1 $\mu$g of total internal mammary artery RNA; 50 mM Tris-HCl pH 8.5; 30 mM KCl; 8 mM $MgCl_2$; 1 mM DTT; 20 units RNAsin from Boehringer Mannheim; 1 mM each of DATP, dTTP, dGTP, and dCTP; 0.5 $\mu$g random hexamers from Boehringer Mannheim; and 40u of ANV reverse transcriptase from Boehringer Mannheim, in a total volume of 20 $\mu$L. This was incubated for 1 hour at 42° C., heat inactivated, and then stored at −80° C. before use. An initial amplification of 10% of the reverse transcriptase reaction was performed with just the sense oligonucleotide primer, known as "H2" and Ampliwax™ PCR Gem 100 beads Perkin Elmer in a "hot start" procedure according to the directions of the manufacturer. The following reagent concentrations were used: 50 mM KCL; 10 mM Tris-HCl at pH 8.3; 1.5 mM $MgCl_2$; 1 mg/mL gelatin; 0.2 mM each of DATP, dTTP, dGTP, and dCTP; 0.1 $\mu$M primer(s); and 2.5 units of Taq polymerase from Boehringer Mannheim or Perkin Elmer in a volume of 100 $\mu$L (these conditions were used thereafter unless noted). The cycling protocol was as follows: 94° C. for two minutes, then 30 cycles of 94° C. for 30 seconds, 45° C. for 1 minute, and 72° C. for 1 minute. A second amplification was then performed on 10% of the primary reaction products using the H2 primer and a degenerate antisense oligonucleotide primer known as "P2B" against the carboxy terminal peptide. The cycling parameters were: 94° C. for two minutes followed by 30 cycles of 94° C. for 30 seconds, 40° C. for 30 seconds, 50° C. for 1 minute and 72° C. for 1 minute. A product was observed of the correct size and following purification by Glass Fog from Bio101, on 2% Biogel agarose from Bio101 was blunt sub-cloned into EcoRV digested BluescriptII SK+vectors from Stratagene and sequenced to high resolution by Sequenase 2.0 from universal primers from United States Biochemical. Five individual clones were sequenced to eliminate any spurious Taq polymerase errors.

The 5' end of the human coding region was amplified using an anchored polymerase chain reaction kit, available under the tradename "5'-Amplifinder RACE" from Clonetech according to the manufacturer's instructions. This method uses single stranded RNA ligase to ligate an anchor oligonucleotide onto the 3' end of appropriately primed first strand cDNA. Templates used were either human heart polyA+RNA obtained from Clonetech or polyA+RNA isolated from primary cultures of human vascular smooth muscle cells obtained from Clonetics. The polyA+RNA from cultured vascular smooth muscle cells was purified with RNAzol B from Biotecx using batch chromatography on Oligo-dT latex beads from Qiagen. Both templates yielded amplified cDNAs and specific subclones were chosen solely by size. First strand RNA templates were prepared by either specific priming or priming with random hexamers from Boehringer Mannheim. In general, the specific primed templates yielded longer clones but could not be used for multiple step wise amplification of the rest of the coding region.

Amplification from anchored templates using the sense anchor primer and appropriate antisense specific primers was accomplished using ampliwax beads from Perkin Elmer and "hot start" polymerase chain reaction using the same reaction conditions as above, but with 0.2 $\mu$M primers in a total volume of 50 $\mu$L. The cycling protocol was as follows: 94° C. for 2 minutes then 30 cycles of 94° C. 45 seconds, 60° C. 45 second, and 72° C. for 1.5 minutes, followed by a final extension of 72° C. for 10 minutes. Following a primary amplification, aliquots (10–20%) of the reactions were run out on 2% Biogel agarose from Bio101 and size selected. After purification by glass fog from Bio101, 1–10% of the elutes were reamplified (2°), usually with a nested primer. Products were observed at this point and purified by glass fog as before and sequenced directly using a thermal cycling kit from New England Biolabs. Once the products were confirmed they were sub-cloned as described above. Between 5 to 8 individual clones from each of three sequential amplifications were sequenced to eliminate spurious Taq polymerase errors and appropriate clones chosen for the finished molecule. A summary of the primer pairs sense/antisense used to amplify the complete coding region:

| position Clone # | Source of Template | 1° | 2° | 5'–3' |
|---|---|---|---|---|
| 6 699-941 | dN6 primed IMA whole RNA | H2 | H2/P2B | |
| 23 231-698 | H2R primed Heart polyA + RNA | AP/H2R | AP/H3 | |
| 117 119-230 | dN6 primed VSMC poly A + RNA | AP/H6 | AP/H6 | |
| 131 | dN6 primed VSMC poly A + RNA | AP/H6 | AP/H7 | 1-118 |

Figure 4:
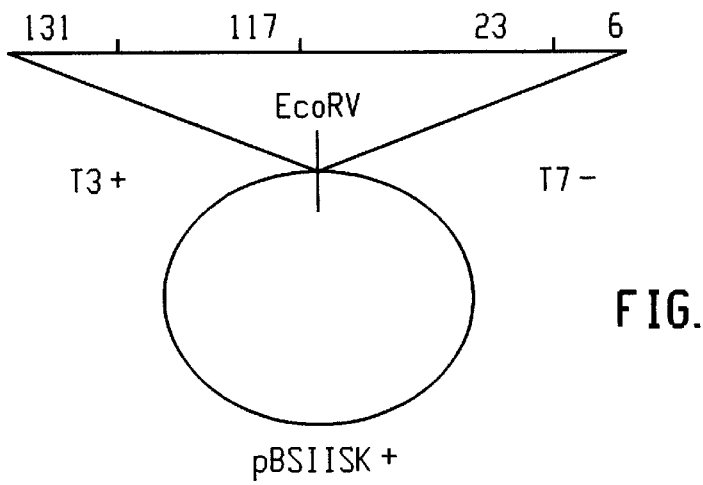
FIG. 4 is a map of human Gax gene showing how the separately cloned fragments were joined and oriented in the plasmid, Bluescript IISK+.

Clones were pieced together 3'-5' as follows: fragments 6 and 23 share engineered BglII sites; fragments 23 and 117 share a native SfaNI site; fragment 117 has a native NcoI site which is compatible with an engineered BspHI site in fragment 131. Both engineered sites have a single base change in the wobble base of leucine codons, as noted on the final sequence as shown in FIG. 3. Once assembled the molecule was excised by digestion with EcoRI and HindIII. The map in FIG. 4 shows the molecule and its orientation.

TABLE 1

Primers Used to Amplify Human Gax gene

| Primer | | Sequence 5'–3' |
|---|---|---|
| P2B | SEQ ID NO:6 | TCA,IA(G/A),(G/A)TG,IGC,(G/A)TG, (T/C)TC |
| H2 | SEQ ID NO:7 | GCGCGC(AGATCT)CAC,TGA,AAG,ACA,GGT,AAA |
| H2R | SEQ ID NO:8 | TT,TAC,CTG,TCT,TTC,AGT,GAG |
| H3 | SEQ ID NO:9 | GCGCGC(AGATCT)AG,ATT,CAC,TGC,TAT,CTC,GTA |
| H6 | SEQ ID NO:10 | GCGCGTGCCCCCTCTGATG,CTG,GCT,GGC,AAA,CAT,GT |
| H7 | SEQ ID NO:11 | GCGCGC(TCTTGA)AGG,GCG,AGA,GAG,GAT,TGG,GA |
| AP | SEQ ID NO:12 | CTGGTTCGGCCCACCTCTGAAGGTTCCAGAATCGATAG |
| Anchor | SEQ ID NO:13 | GGAGACTTCCAAGGTCTTAGCTATCA(CTTAAG)CAC |

Engineered enzyme sites are bracketed.

The Gax Gene Maps to a Novel Locus on Chromosome 7 in the Human Genome

To determine the map location of Gax in the human genome, a 16.5 kilobase pair fragment of the human genomic Gax gene in λFix II from Stratagene was purified with a Qiagen purification column according to the directions of the manufacturer, and it was labeled with biotin 11-dUTP by nick translation. Metaphase spreads of normal human lymphocytes were prepared according to the methods of Fan, Y., Proc. Natl. Acad. Sci. (USA) Vol. 87, pp. 6223–6227 (1990). Fluorescence in situ hybridization and immunofluorescence detection were performed according to the methods of Pinkel, D., et. al., Proc. Natl. Acad. Sci. (USA) Vol. 83, pp. 2934–2938 (1986) and Testa, J. R., et al. Cytogenet. Cell. Genet. Vol. 60, pp. 247–249 (1992). Chromosome preparations were stained with diamidino-2-phenylindole and propidium iodide according to Fan, Y. S., et. al., Proc. Natl. Acad. Sci. (USA) Vol. 87, pp.6223–6227 (1990).

Forty metaphase spreads were examined with a Zeiss Axiophot fluorescence microscope, and fluorescent signals were detected on the short arm of chromosome 7 in 34 of these spreads. All signals were located at p15->p22, with approximately 70% of the signals at 7p21. Based on these data, Gax is the only homeoprotein known to map to this locus.

Gax Gene Expression is Down-regulated in Cultured Vascular Smooth Muscle Cells Upon Mitogen Stimulation It has been found that the Gax gene is expressed in quiescent vascular smooth muscle cells. Since platelet derived growth factor hereinafter also referred to as "PDGF" and other growth factors regulate vascular smooth muscle proliferation and differentiation, differences in Gax gene expression in response to PDGF and other mitogens such as fetal calf serum were examined in cultured vascular myocytes.

Cultures of rat smooth muscle cells were obtained from the media of aortas isolated from adult male Sprague-Dawley rats. Cells were seeded onto dishes in medium containing a 1:1 mixture of Dulbecco's modified Eagle's medium and Ham's F12 and supplemented with 10% newborn calf serum. Once established, the cells were maintained at 37° C. in a humidified atmosphere of 5% carbon dioxide, and subcultured within three days after reaching confluence. Vascular smooth muscle cells were labeled with monoclonal antibodies to smooth muscle α-actin from Sigma Chemical Co. to verify identity.

The cultured cells were exposed to various mitogens as discussed below. The cells were then harvested and the total mRNA was extracted. The total RNA from rat cultured cells was prepared by the guanidine thiocyanate method according to Chomcynzski, P., and N. Sacchi, (1987) "Single-step Method of RNA Isolation by Acid Guanidinium Thiocyanate-phenol-chloroform Extraction" Anal. Biochem. Vol. 162, pp. 156–159, fractionated on 1.2% agarose gels containing formaldehyde, and blotted onto nylon membranes. The RNA from cultured cells was separated on 30-cm gels for transcript size determination and on 10-cm gels for other studies. Hybridizations were carried out at 65° C. in buffer containing 0.5 M sodium phosphate at pH 7.0, 7% sodium dodecyl sulfate, 1 mM EDTA, and 1% bovine serum albumin, using a cDNA probe labeled by random priming consisting of a truncated Gax cDNA lacking the 5' end and the CAX repeat, where the X may be cytosine or guanine. Probes for Hox-1.3 and Hox-1.4 consisted of the cDNAs isolated from the rat aorta library, and the probe for Hox-1.11 consisted of the DraI-EcoRI fragment of its cDNA. The blots were washed with a final stringency of 0.1 to 0.2×SSC-0.1% sodium dodecylsulfate at 65° C. After the probings with the homeobox probes were complete, the blots were rehybridized with a probe to rat glyceraldehyde 3-phosphate dehydrogenase hereinafter also referred to as "GAPDH," to demonstrate message integrity. Gax mRNA and GAPDH mRNA were quantified with a Molecular Dynamics model 400S PhosphorImager to integrate band intensities, or by scanning densitometry of autoradiograms. In all quantitative comparisons of Gax mRNA levels between experimental groups, Gax mRNA levels were normalized to the corresponding GAPDH level determined on the same blot, to account for differences in RNA loading.

Time Course of GAX Down-regulation in Cultured Vascular Smooth Muscle Cells

Rat vascular smooth muscle cells, grown to a greater than about 90% confluence, were placed in low-serum medium containing 0.5% calf serum for 3 days, to induce quiescence. At this time, the medium was removed from the cells and replaced with fresh medium containing either 10% fetal calf serum or 10 ng/ml platelet derived growth factor from human platelets. The cells were then incubated for the various times in the presence of either the fetal calf serum or the PDGF. As a control, quiescent cells were incubated with fresh serum-free medium alone. The cells exposed to PDGF were harvested at 0.25, 0.5, 1, 2, and 4 hours, and the cellular RNA isolated. The cells exposed to human fetal calf serum were harvested at 4, 24, and 48 hours. The Gax and the Hox mRNA levels were determined by Northern blot analysis. Typical results are shown in FIGS. 5A and 5B.

Figure 5A:
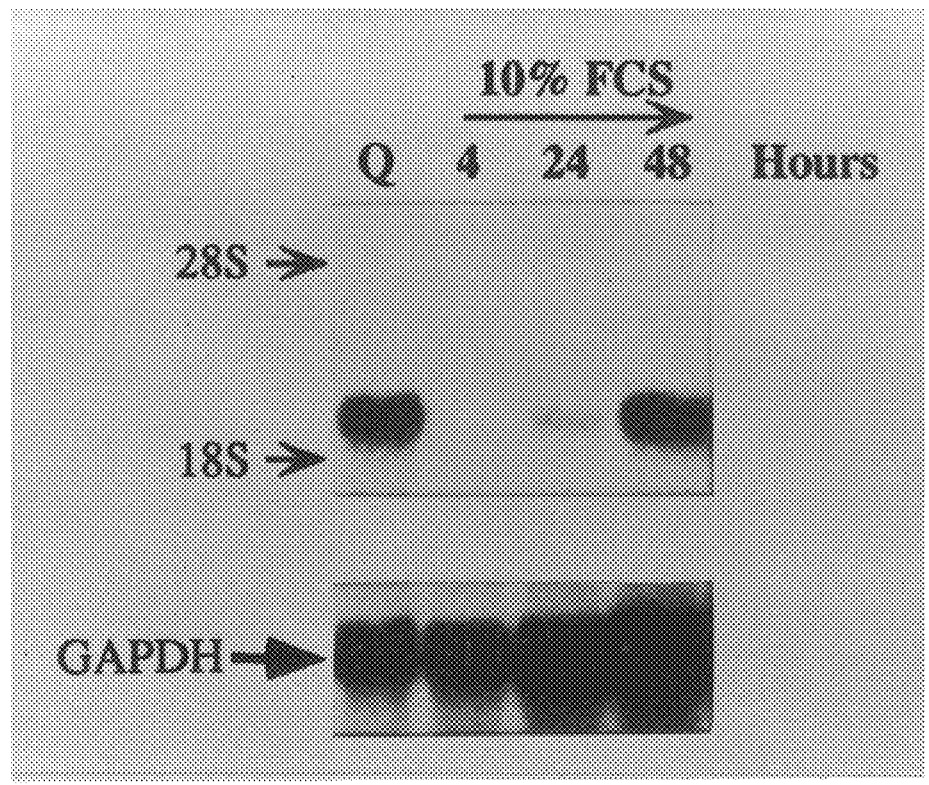
FIG. 5A is a northern blot showing Gax RNA levels in vascular smooth muscle cells in response to 10% fetal calf serum after 4, 24, and 48 hours; lane Q is RNA from quiescent cells; GAPDH is rat glyceraldehyde 3-phosphate dehydrogenase.
Figure 5B:
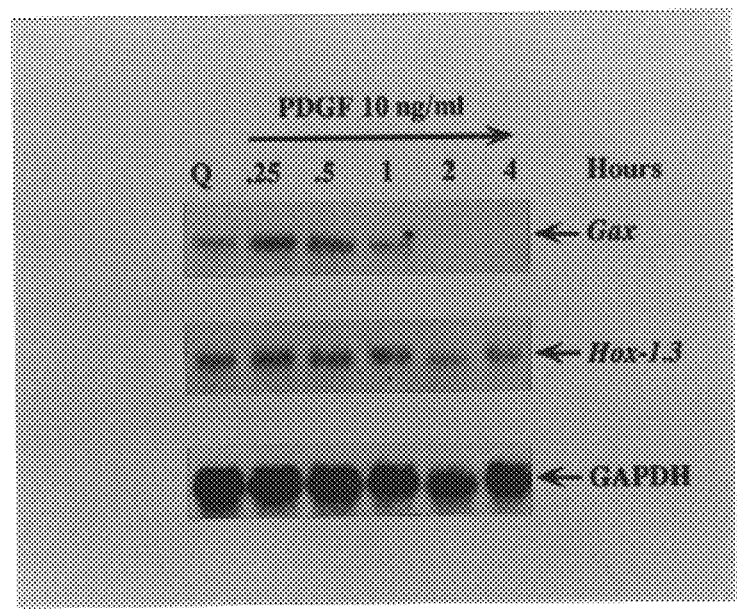
FIG. 5B is a northern blot showing Gax RNA levels and Hox 1.3 RNA levels in vascular smooth muscle cells in response to 10 ng/ml human platelet derived growth factor at 0.25, 0.5, 1, 2, and 4 hours, lane Q is RNA from quiescent vascular smooth muscle cells.

A rapid down-regulation, that is a reduction in the amount of Gax mRNA, occurred in the vascular smooth muscle cells when they were stimulated with either fetal calf serum or PDGF as shown in FIGS. 5A and 5B. The down-regulation ranged from 5- to nearly 20-fold, depending on the mitogen used and the experiment. The down-regulation typically occurred within 2 hours after stimulation with fetal calf serum or PDGF, and was maximal at 4 hours. Gax mRNA transcript levels began to recover significantly by approximately 24 hours and approached baseline between 24 and 48 hours after stimulation. The rate of recovery varied with the magnitude of the initial down-regulation and the individual cell culture preparations. While PDGF isolated from human platelets caused a rapid down-regulation of Gax, it had little or no effect on Hox-1.3 mRNA levels. Neither fetal calf serum nor any of the three isoforms of PDGF showed any effect on the transcript levels of Hox-1.3, Hox-1.4, or Hox-1.11, homeobox genes which were also isolated from the vascular smooth muscle library.

Magnitude of Gax Down-regulation Correlates With Potency of Mitogen

PDGF is a homodimer or heterodimer made of various combination of two chains, A and B. Thus, there are three isoforms of PDGF; PDGF-AA; PDGF-AB; and PDGF-BB; and they have differing potencies for stimulating DNA synthesis in rat vascular smooth muscle cells. The PDGF-AA, PDGF-AB and PDGF-BB were compared for their effect on Gax expression. Quiescent rat vascular smooth muscle cell received 10 ng/ml of either PDGF-AA, PDGF-AB, PDGF-BB, or 10% fetal calf serum. After 0, 1, 2, 4 and 8 hours the cells were harvested and the Gax mRNA level determined. The results are shown in FIG. 6.

Figure 6:
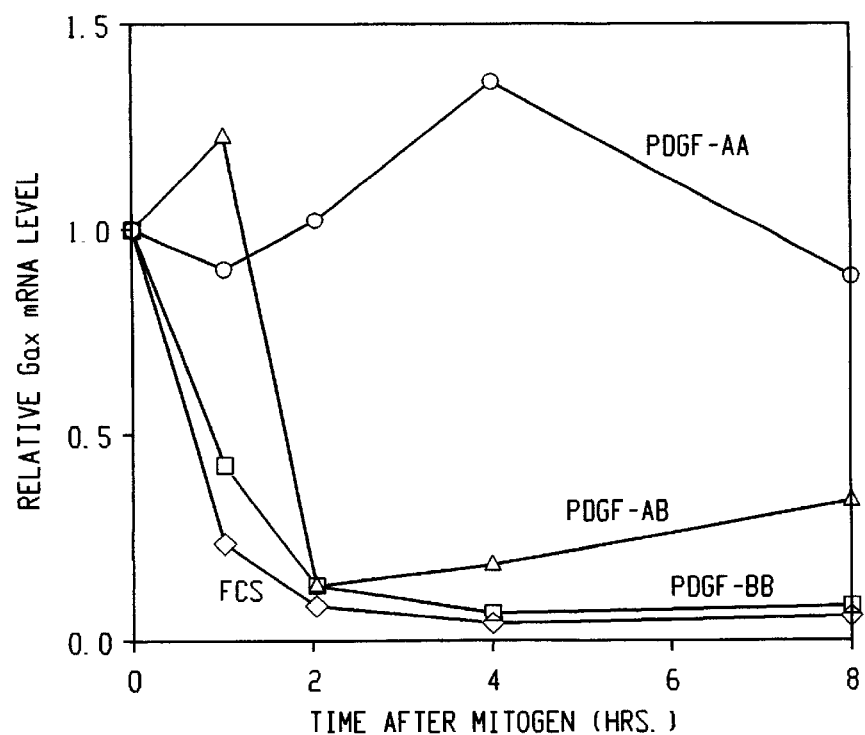
FIG. 6 is a graph of changes in relative Gax mRNA levels in vascular smooth muscle cells in response to 10% fetal calf serum and 10 mg/ml of the PDGF isoforms; the circles represent PDGF-AA, the squares represent PDGF-BB, the diamonds represent fetal calf serum, and the triangles represent PDGF-AB.

As shown in FIG. 6, PDGF-AA did not down-regulate Gax gene expression in vascular smooth muscle cells, whereas the PDGF-AB and PDGF-BB isoforms, and the fetal calf serum reduced Gax gene expression approximately 10-fold by 4 hours. The greatest down-regulation occurred with the fetal calf serum followed by that with PDGF-BB and PDGF-AB.

Figure 7:
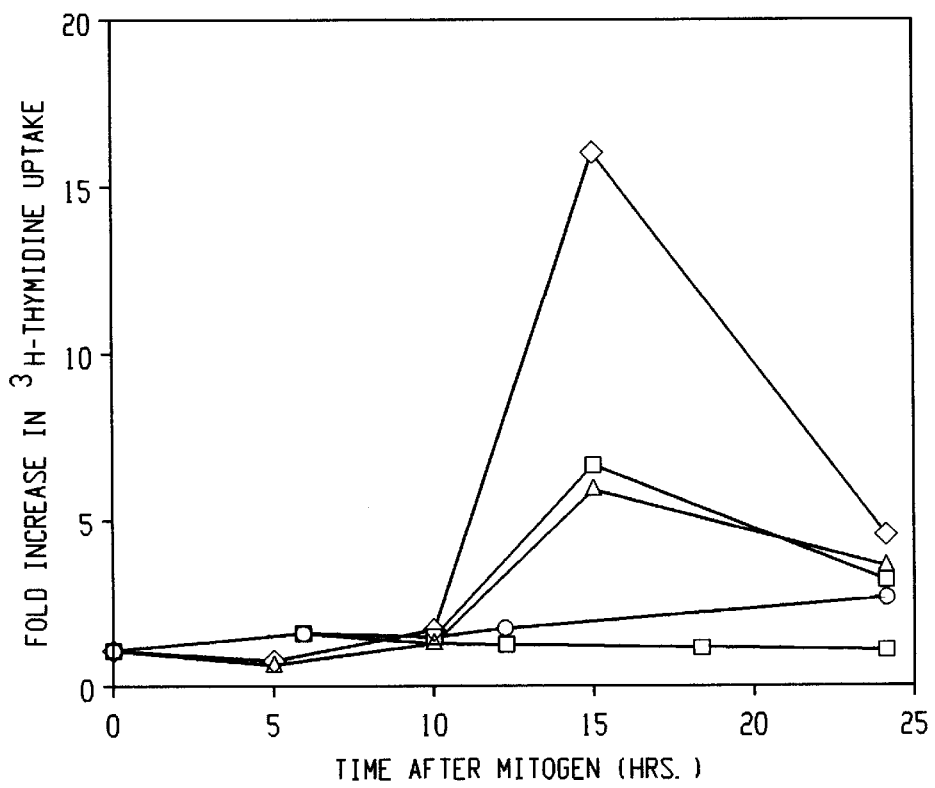
FIG. 7 is a graph showing $^3$H-thymidine uptake in vascular smooth muscle cells at various times after stimulation with fetal calf serum and PDGF isoforms; the circles represent PDGF-AA, the triangles represent PDGF-AB, the squares represent PDGF-BB, the diamonds represent fetal calf serum, and the solid squares represent no mitogen.

To determine whether the extent of Gax gene down-regulation correlated with the potency of the mitogen used to stimulate the vascular smooth muscle cells, the ability of the three PDGF isoforms and fetal calf serum to stimulate DNA synthesis was measured by $^3$H-thymidine uptake. Quiescent vascular smooth muscle cells were stimulated with one of the three PDGF isoforms, at 10 mg/ml, or 10% fetal calf serum. Then 5 $\mu$Ci/ml $^3$H-thymidine was added to the cultures for 1 hour at various time points as shown in FIG. 7. The cells were harvested and the $^3$H-thymidine uptake was measured. The results are shown in FIG. 7.

The PDGF-AA at 10 ng/ml, which was ineffective in causing Gax gene down-regulation, only weakly stimulated DNA synthesis as shown in FIG. 7. PDGF-AB and PDGF-BB both stimulated cell proliferation as measured by $^3$H-thymidine uptake at 15 hours. However, the fetal calf serum which was most effective at down regulating Gax gene expression, was also the most effective mitogen, that is it demonstrated the greatest $^3$H-thymidine uptake.

Down-regulation of the Gax gene is Dependent on the Dose of the Mitogen

Figure 8:
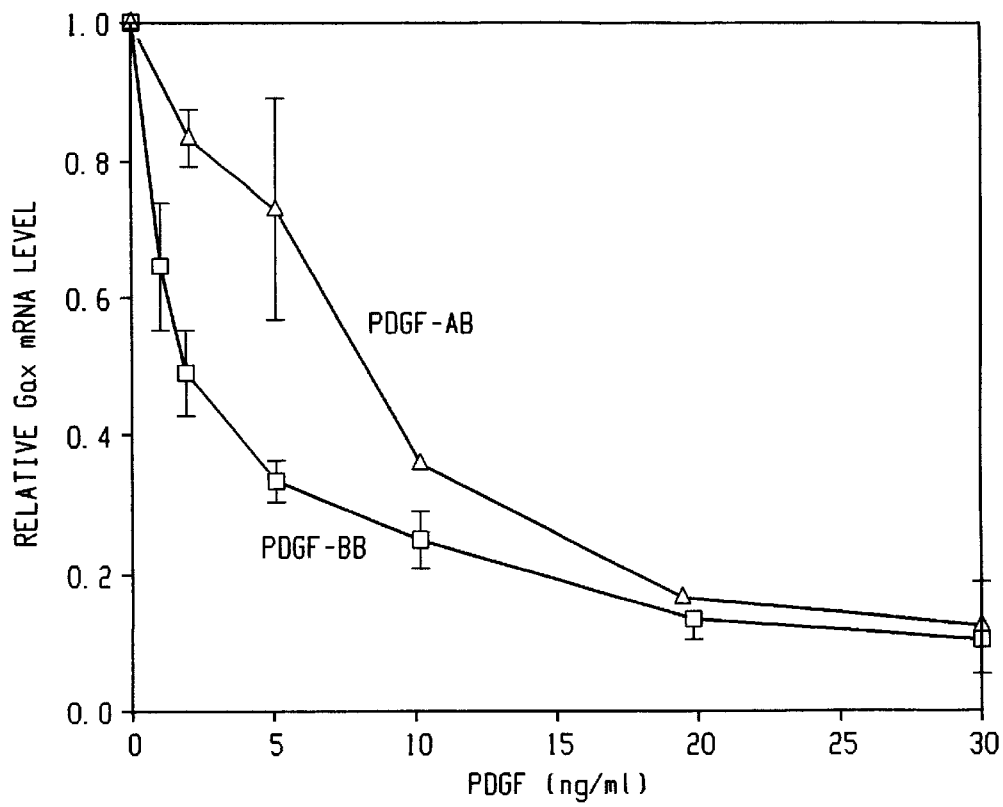
FIG. 8 is a graph showing relative Gax mRNA levels in vascular smooth muscle cells in response to varying doses of PDGF-AB, represented by triangles, and PDGF-BB, represented by squares.
Figure 9:
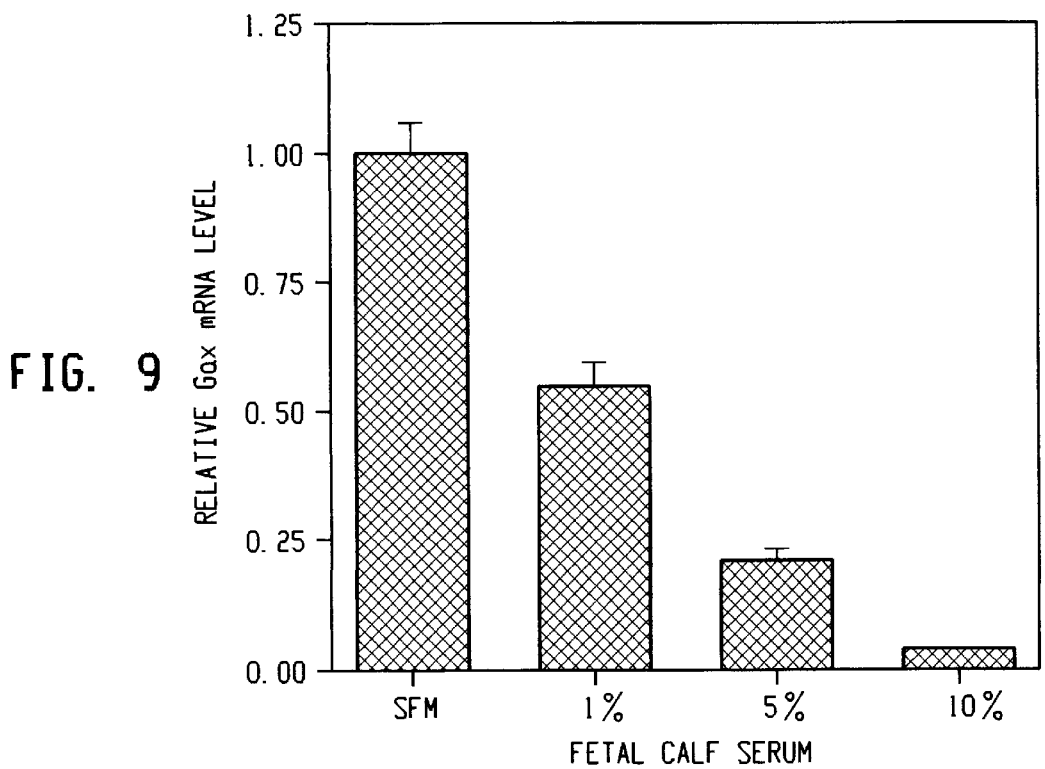
FIG. 9 is a graph showing relative Gax mRNA levels in vascular smooth muscle cells in response to varying doses of fetal calf serum.

Dose-response experiments were conducted by stimulating quiescent vascular smooth muscle cells with either PDGF-AB, PDGF-BB or fetal calf serum at varying doses as shown in FIGS. 8 and 9. The effects on Gax mRNA levels were measured at 4 hours after mitogen stimulation. The results are shown in FIGS. 8 and 9.

As shown in FIG. 8, the dose response curves reveal that the 50% effective dose for Gax gene down-regulation 4 hours after PDGF-AB stimulation is between 4 and 8 ng/ml. The 50% effective dose for Gax gene down regulation 4 hours after PDGF-BB stimulation is between 2 and 5 ng/ml. The 50% effective dose for Gax down regulation 4 hours after fetal calf serum is approximately 1%, as shown in FIG. 9. Furthermore, 10% fetal calf serum suppresses Gax mRNA levels nearly 20-fold at 4 hours, an effect larger than that of a maximal stimulatory dose of PDGF-BB (30 ng/ml), which has a 10-fold effect, or of PDGF-AB, which has a less than 8-fold effect, as shown in FIG. 6. Thus, the down-regulation of Gax gene induced by either fetal calf serum or the different isoforms of PDGF correlates well with their abilities to stimulate DNA synthesis as measured by $^3$H-thymidine uptake.

The Gax gene down-regulation is sensitive to low levels of mitogen stimulation, which cause a significant decrease in Gax mRNA levels. As shown in FIG. 9, stimulation of quiescent rat vascular smooth muscle cells with 1% fetal calf serum caused a 40% decrease in Gax mRNA levels after 4 hours. However, such stimulation increased $^3$H-thymidine uptake less than two-fold over that observed in quiescent vascular smooth muscle cells (data not shown). Treatment with PDGF-BB at doses as low as 2 ng/ml, also caused a detectable decrease in the Gax mRNA level.

Gax Expression is Up-regulated or Induced when Synchronously Growing Cells are Deprived of Serum Sparsely plated vascular smooth muscle cells were grown in a medium containing 20% fetal calf serum, and then placed into serum free medium. The RNA was harvested at various times from 0 to 25 hours. The total mRNA was extracted and subjected to Northern Blot Analysis, then the mRNA transcript of Gax was quantified.

Figure 10:
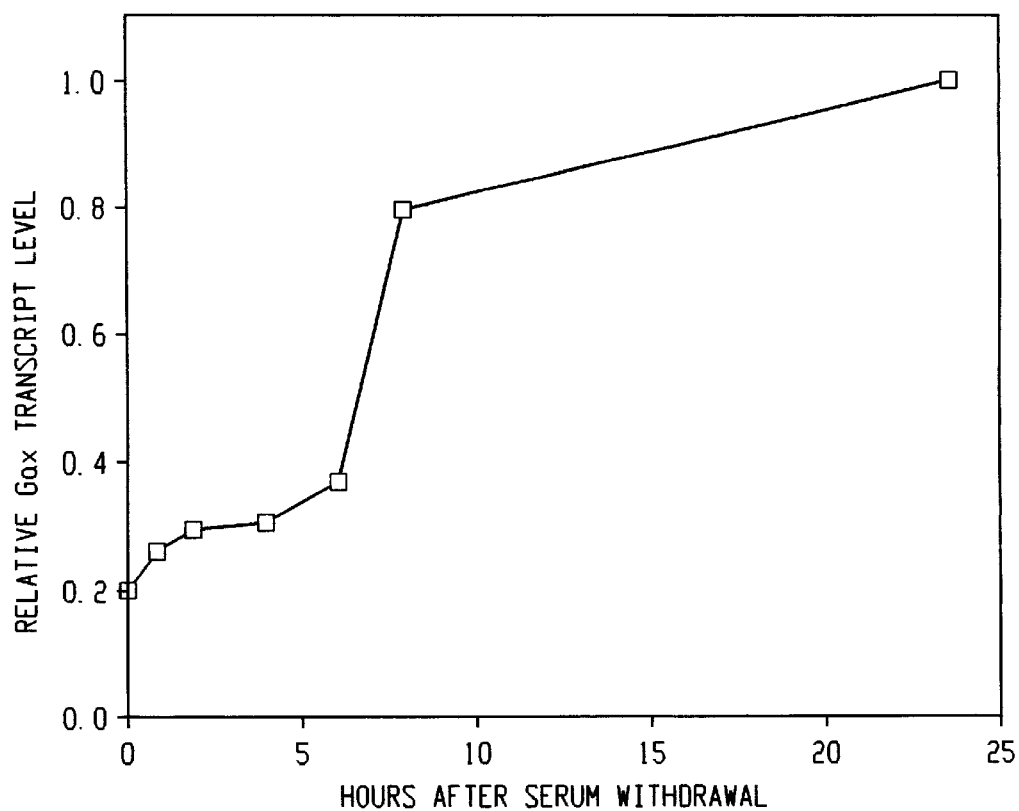
FIG. 10 is a graph showing relative Gax mRNA levels in vascular smooth muscle cells in response to fetal calf serum withdrawal.

As shown in FIG. 10, the expression of the Gax gene was induced fivefold in vascular smooth muscle cells within 24 hours after the rapidly growing cells were placed. in the serum-free medium. Thus, expression of Gax gene is regulated by the growth state of the cell, and its down-regulation is a prominent feature of the $G_0/G_1$ transition in these cells.

Gax Protein Inhibits Mitogen-Induced S Phase Entry in Vascular Smooth Muscle Cells Production of Recombinant Proteins To determine whether Gax gene exerts a negative control on cell growth in vascular smooth muscle cells, Gax gene was expressed as a glutathione S-transferase (hereinafter also referred to as "GST") fusion protein in bacteria and microinjected it into quiescent vascular smooth muscle cells. To determine the effect of the Gax protein on serum-induced cell proliferation, the effect of GST-Gax protein was compared to the effect of known protein regulators of cell growth.

To produce the Gax protein evaluated herein, the cDNA coding regions for Gax was fused in frame to the pGEX-2T expression vector obtained from Pharmacia Biotechnology, and then expressed in *E. coli*. Specifically, GST-Gax was produced according to the following procedure: the coding region of Gax cDNA spanning from nucleotides 200–1108 was amplified by polymerase chain reaction methods using the following primers:

5'GCGCGCGTCGACGAACACCCCCTCTTTGGC 3' SEQ ID NO: 14 and

5'GCGCGCAAGCTTTCATAAGTGTGCGTGCTC 3' SEQ ID NO: 15

The resulting DNA was digested with SalI and HindIII restriction enzymes and cloned into SalI and HindIII sites in the polylinker of pGEM3-1T in vitro transcription translation vector described in Patel R. C. and Sen G. C. (1992) "Identification of the Double-stranded RNA-binding Domain in the Human Interferon-inducible Protein Kinase," *J. Biol. Chem.* Vol. 267; pp. 7671–7676. The BamHI to NaeI fragment of pGEM3-1T containing the Gax coding region was then sub-cloned into the same sites of pGEX-2T. The pGEX-2T vector with the YY1 cDNA, used to produce GST-YY1, was from Thomas Shenk at Princeton University.

The resultant glutathione S-transferase fusion proteins were purified by affinity chromatography on glutathione-agarose beads. *E. coli* XL1-blue cells were then transformed with the appropriate plasmid and were grown to a density of 0.6–0.8 $A_{600}$ and induced with 0.5 mM isopropyl-B-D-thiogalectopyrenoside for 2 hours. The cells were harvested and lysed by ultrasonic vibration in phosphate buffered saline containing 1% triton x-100, 1 mM PMSF and 5 μg/ml aprotinin. The lysate was centrifuged at 15,000×g and the supernatant was collected. The supernatant was bound to the glutathione sepharose from Pharmacia (0.5 ml of resin per 100 ml of bacterial culture) for 2 hours on a rotator at 25 rpm. The slurry was pelleted by centrifugation at 1000×g for 2 minutes, then washed twice with complete lysis buffer then washed twice with lysis buffer lacking triton x-100. The bound protein was eluated for 30 minutes with phosphate buffered saline containing 10 mM reduced glutathione, from Sigma Chemical Company, 40 mM DTT and 150 mM NaCl. Purity of the GST-Gax protein was greater than 90% as determined by SDS-PAGE gels stained with Coomassie blue.

To produce recombinant MHox, its cDNA was fused in frame to the pQE-9 *E. coli* expression vector obtained from Qiagen, Inc., Chatsworth, Calif., then expressed in bacteria, and .purified by adsorption to a nickel column.

For microinjection, proteins were concentrated in a buffer containing of 20 mM Tris, 40 mM KC1, 0.1 mM EDTA, 1 mM β-mercaptoethanol, and 2% glycerol using Centricon-30 from Amicon microconcentrators. Concentrated proteins were stored in this buffer in aliquots at −80° C.

Microinjection and Cell Culture Methods

Microinjections were performed using a semiautomatic microinjection system from Eppendorf Inc. in conjunction with a Nikon Diaphot phase contrast microscope. According to Peperkole, R., et al. (1988) *Proc. Natl. Acad. Sci. USA* Vol. 85, pp. 6758–6762, The injection pressure was set at 70–200 hPa and the injection time was 0.3 to 0.6 seconds.

After injection, cells were stimulated 24 hours with medium containing 10% fetal calf serum, and the incorporation of 5'-bromo-2'-deoxyuridine, hereinafter also referred to as "BrdU" was measured with a cell proliferation kit according to the directions of its manufacturer, Amersham. When fetal calf serum-stimulated BrdU labeling was determined, BrdU was included for 24 hours with the medium used to stimulate the cells. Where the ability of microinjected proteins to stimulate growth in serum-poor medium was measured, cells were incubated 24 hours in the same low serum medium used to induce quiescence, but supplemented with BrdU. After labeling, the cells were fixed with acid-ethanol, and the percentage of nuclei positive for BrdU uptake was determined for protein-injected and buffer-injected cells. The percent of cell growth inhibition was calculated according to the following formula:

$$\% \text{ Inhibition} = \frac{\frac{CL}{CT} - \frac{IL}{IT}}{\frac{CL}{CT}} \times 100$$

where IL represents the number of injected labeling positive for BrdU; IT, the total number of injected cells; CL the number of control-injected cells labeling with BrdU; CT, the total number of control-injected cells counted. With this equation, inhibition of mitogen-induced entry into S phase is represented by a positive number and stimulation of cell growth is represented by a negative number.

Evaluation of Gax Protein

To determine if the Gax protein inhibits the entry of mitogen stimulated vascular smooth muscle cells into S-phase, the effect of the Gax protein was compared to proteins known to effect cell proliferation, and to control proteins. Such comparison proteins include a neutralizing antibody against ras, "Y13-259," which is highly effective in blocking S phase entry when microinjected into NIH3T3 cells; the transcription factor MHox, a homeodomain protein unlikely to have an inhibitory effect on cell proliferation; and YY1, a zinc finger transcription factor unlikely to have a negative effect on cell growth.

Quiescent rat vascular smooth muscle cells were microinjected with either 0.6 mg/ml GST-Gax protein; 1.6 mg/ml MHox; 1.2 mg/ml YY1; 8 mg/ml Y13-259; 2mg/ml GST alone; or 8 mg/ml mouse anti-human IgG. The cells were then stimulated for 24 hours with 10% fetal calf serum in medium containing BrdU. After 24 hours, the fraction of nuclei labeling with BrdU was determined and percentage inhibition of S-phase entry calculated. The results are summarized in Table 2.

TABLE 2

Effect of Microinjected Proteins on the Serum-induced Proliferation of Vascular Smooth Muscle Cells

| Treatment | Number of Experiments | Total Number of Cells Examined | Mean % Inhibition of FCS-stimulated Growth ± Standard Error |
|---|---|---|---|
| Antibody Y13-259 | 2 | 328 | 60.8 ± 3.9 |
| Mouse anti-human | 3 | 330 | −3.4 ± 4.5 |

TABLE 2-continued

Effect of Microinjected Proteins on the Serum-induced Proliferation of Vascular Smooth Muscle Cells

| Treatment | Number of Experiments | Total Number of Cells Examined | Mean % Inhibition of FCS-stimulated Growth ± Standard Error |
|---|---|---|---|
| IgG | | | |
| GST-Gax | 15 | 2943 | 42.7 ± 3.3 |
| MHox | 2 | 236 | −5.3 ± 9.3 |
| GST-YY1 | 5 | 306 | 0.0 ± 12.2 |
| GST | 7 | 1144 | −2.6 ± 2.1 |

FCS—fetal calf serum
BrdU labeling of quiescent vascular smooth muscle cells was 10.1 ± 1.2% (N = 12, total number of cells counted = 2659); for uninjected FCS-stimulated vascular smooth muscle cells, 54.8 ± 2.4% (N = 27, total number of cells counted = 4282); and for sham-injected FCS-stimulated cells, 49.6 ± 2.5% (N = 27, total number of cells injected = 3401).

As shown in Table 2, the GST-Gax protein inhibited vascular smooth muscle cell entry into S-phase by 42.7%. The GST Gax protein effect on mitogen-stimulated entry into S phase is specific. The other injected proteins GST, YY1, MHox and the mouse anti-human IgG failed to inhibit vascular smooth muscle cell growth. In comparison to the GST-Gax protein, the antibody Y13-259, as anticipated, significantly decreased mitogen-induced cell proliferation. Vascular smooth muscle cells microinjected with Y13259 demonstrated a 61±4% decrease in cell entry into S-phase.

Gax Protein Inhibits Vascular Smooth Muscle Cell Proliferation in a Dose-Dependent Manner.

To determine the concentration of microinjected GST-Gax required to inhibit vascular smooth muscle cell growth, solutions containing different concentrations of GST-Gax protein were microinjected into quiescent vascular smooth muscle cell and the effects on mitogen-stimulated entry into S phase examined. Specifically, vascular smooth muscle cells were rendered quiescent by incubation in medium containing 0.5% calf serum for three days. The cells were microinjected with varying concentrations of GST-Gax, and stimulated with 10% fetal calf serum, and labeled with BrdU. After 24 hours, the percentage inhibition of cell proliferation was determined. Each data point represents the mean±standard error of 3–5 experiments in which 100–200 cells per experimental group were injected.

Figure 11:
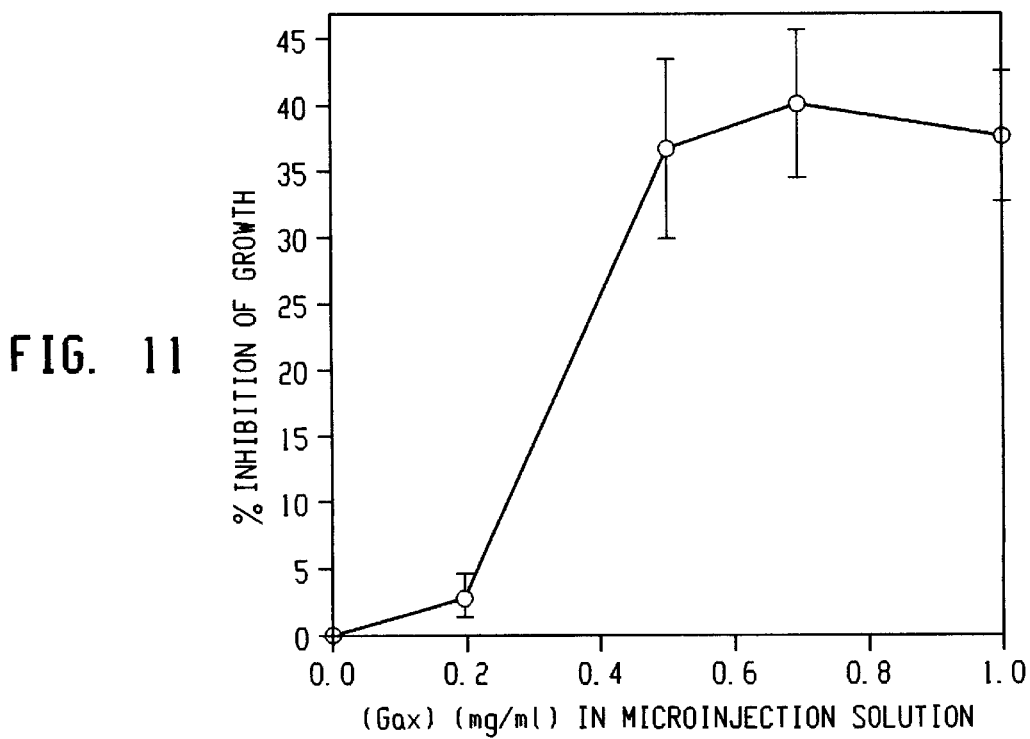
FIG. 11 is a dose response curve showing % inhibition of growth in vascular smooth muscle cells in response to varying doses of microinjected GST-Gax protein.

As shown in FIG. 11, the cellular growth inhibition by the GST-Gax protein is dose dependent. Little or no growth inhibition was observed when 0.2 mg/ml GST-Gax protein was injected. The maximal growth inhibition was obtained with approximately 0.5 mg/ml of the GST-Gax protein.

Gax Inhibits Proliferation of Several Cell Types

To determine whether the GST-Gax protein inhibits growth in other cells types, the GST-Gax protein was microinjected into quiescent SV40-transformed vascular smooth muscle cells, BALBc3T3 cells, NIH3T3 cells, human vascular smooth muscle cells, and human fibroblasts. The SV40 transformed cell line was derived from rat vascular smooth muscle cells transformed with the SV40 large T antigen. These cells, while immortalized, retain many differentiated characteristics of untransformed vascular smooth muscle cells. The cells were microinjected with either 0.6 mg/ml GST-Gax protein or 2 mg/ml GST were then stimulated with 10% fetal calf serum, and labeled for 24 hours with BrdU. The results are shown in Table 3.

TABLE 3

EFFECT OF MICROINJECTED GST-GAX PROTEIN ON CELL PROLIFERATION IN DIFFERENT CELL TYPES

| Cell type | GST-GAX protein | Number of Experiments | Number of Cells Examined | Mean & Range Inhibition of FCS-Stimulated Growth | Mitotic Index in Response to FCS |
|---|---|---|---|---|---|
| SV40-transformed VSMC | Yes | 4 | 448 | 27.2 ± 2.0 | — |
| SV40-transformed VSMC | No | | | N/A | 0.60 ± 0.02 |
| BALB/c 3T3 cells | Yes | 4 | 464 | 30.5 ± 10.9 | — |
| BALB/c 3T3 cells | No | | | N/A | 0.64 ± 0.03 |
| NIH3T3 cells | Yes | 4 | 420 | 23.2 ± 1.8 | — |
| NIH3T3 cells | No | | | N/A | 0.70 ± 0.02 |
| Human VSMC | Yes | 3 | 506 | 46.6 ± 8.1 | — |
| Human VSMC | No | | | N/A | 0.33 ± 0.02 |
| Human fibroblasts | Yes | 3 | 336 | 44.5 ± 2.1 | — |
| Human fibroblasts | No | | | N/A | 0.36 ± 0.01 |

FCS - fetal calf serum
VSMC - vascular smooth muscle cells

SV40—transformed vascular smooth muscle cell proliferation was inhibited by GST-Gax protein, as shown in Table 3. The GST-Gax protein also inhibited the proliferation of fibroblast cell lines NIH3T3 and BALB/c 3T3. GST-Gax protein also inhibited the proliferation of human cells, specifically human vascular smooth muscle cells and human foreskin fibroblasts. These results indicate that Gax action is not cell type-specific, although there are differences in the extent inhibition among the different cell types. Among the human cells, the GST-Gax protein exhibits maximal inhibition in vascular smooth muscle cells, the cell type in which the Gax gene is normally expressed. Similarly among the rat cells, the GST-Gax protein exhibits maximal inhibition in vascular smooth muscle cells, the cell type in which the Gax gene is normally expressed.

An Oncogenic Ras Protein Can Reverse Growth Inhibition Caused by the Gax protein To characterize the mechanism of the growth inhibition conferred by the GST-Gax protein, the effects of GST-Gax protein and the transforming oncoprotein, the ras mutant Ras(Leu-61) were compared by microinjecting these proteins into rat vascular smooth muscle cells. A solution containing both 0.5 mg/ml GST-Gax protein and 0.5 mg/ml Ras(Leu-61) was microinjected into quiescent vascular smooth muscle cells. For comparison, other vascular smooth muscle cells received either 0.5 mg/ml GST-Gax protein or 0.5 mg/ml Ras(Leu-61) or 0.5 mg/ml GST. The injected cells were then incubated for 24 hours with medium containing 10% fetal calf serum and BrdU. The results are shown in FIG. 12.

Figure 12:
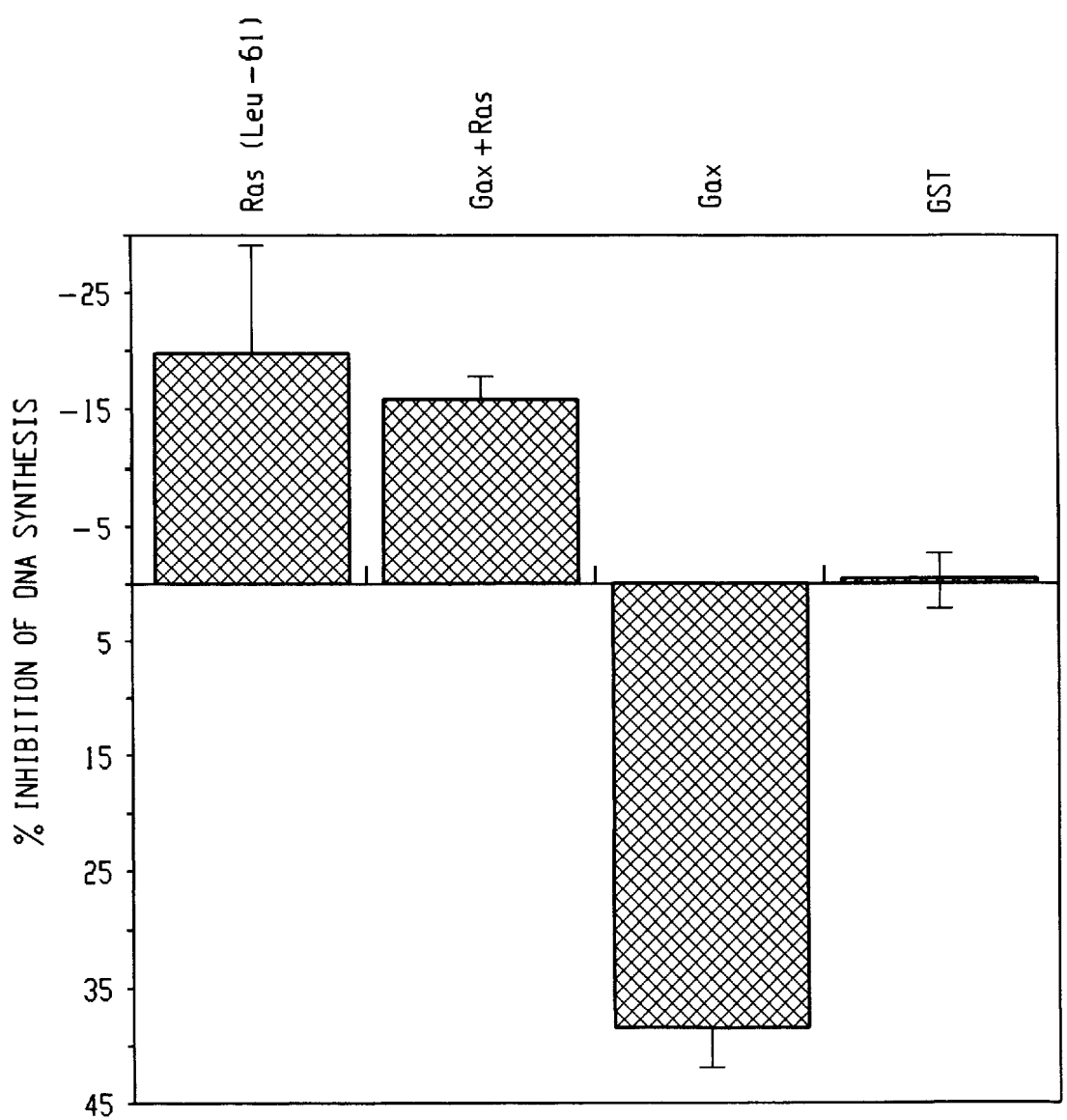
FIG. 12 is a graph showing percent inhibition of mitogen induced DNA synthesis in vascular smooth muscle cells in response to: ras (Leu-61) protein; ras (Leu-61) protein in combination with the GST-Gax protein; GST-Gax protein; and the GST.

As shown in FIG. 12, when Ras(Leu-61) alone was injected, there was an increase in BrdU-labeling as compared to both control-injected cells. In cells injected with GST-Gax protein, growth was inhibited 39%. When the GST-Gax protein and Ras(Leu-61) were coinjected in the cells, the Ras(Leu-61) reversed the growth inhibitory effects of the GST-Gax protein, and the percentage of cells staining positive for BrdU in cells receiving both the Ras(Leu-61) and GST-Gax protein were nearly identical to that observed in cells receiving just the Ras(Leu-61). Thus, the Ras oncoprotein completely reversed the effect of the GST-Gax protein establishing that the presence of GST-Gax protein is not toxic to cells.

The Gax Protein Inhibits Cell Growth when Microinjected Before the G1 to S Boundary To determine the point in the cell cycle when the Gax gene exerts its growth inhibitory effects, the time of S phase on set was determined in rat vascular smooth muscle cells. The vascular smooth muscle cells were stimulated with 10% fetal calf serum and pulse labeled with 10 mCi/ml $^3$H-thymidine for one hour at different times after stimulation. Serarate cultures of the cells were microinjected with GST-Gax protein at various times after receiving 10% fetal calf serum and labeled with BrdU between 10 and 24 hours after receiving the fetal calf serum. Percent inhibition of S-phase entry was determined at each time point. The results are shown in FIG. 13.

Figure 13:
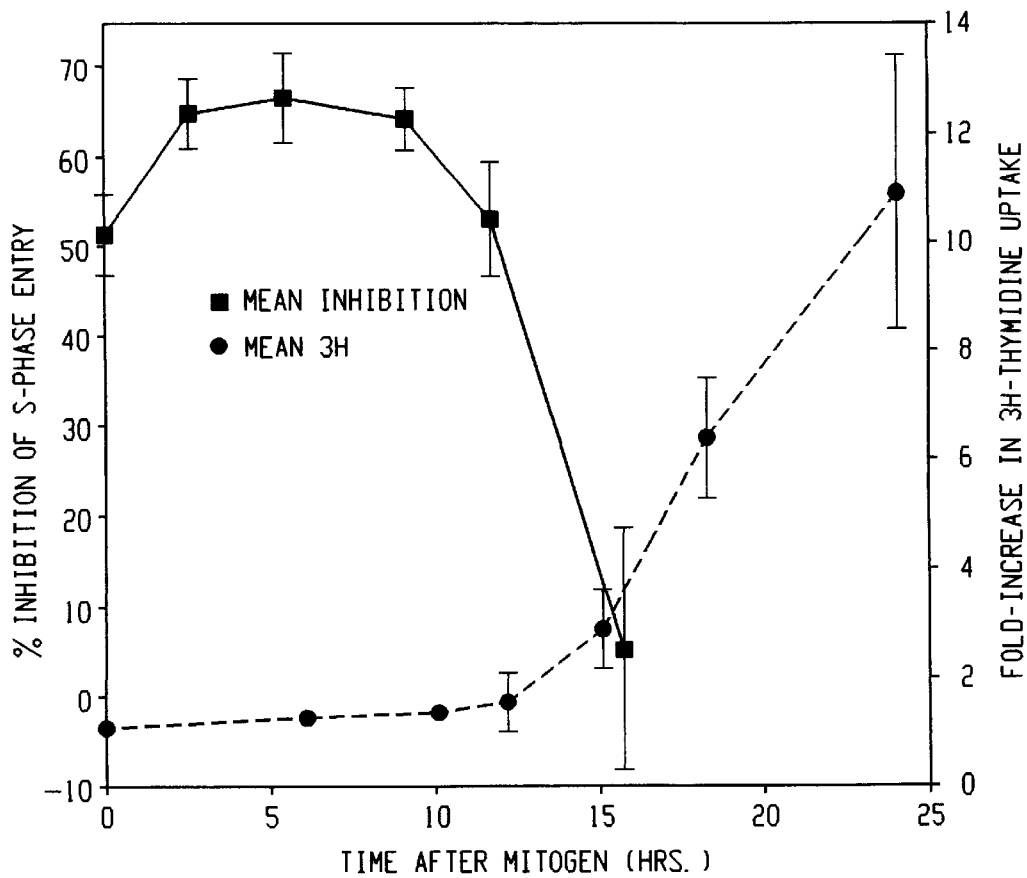
FIG. 13 is a graph showing percent inhibition of vascular smooth muscle cell entry into S phase by microinjected GST-Gax protein over time and the $^3$H-thymidine uptake over the same time period.

As shown in FIG. 13, S phase onset, indicated by the uptake of $^3$H-thymidine, occured at approximately 16–18 hours after mitogen stimulation. GST-Gax protein significantly inhibited vascular smooth muscle cell entry into the S phase when microinjected at any time from stimulation up until approximately 12 hours. However, GST-Gax protein was ineffective when injected at 15 hours. Thus it appears that the Gax gene inhibits a critical step in cell cycle progression prior to the $G_1/S$ boundary; perhaps before the restriction point in $G_1$ where eukaryotic cells are irreversibly committed to entering the S phase.

Gax Gene Expression is Rapidly Down Regulated in Vivo Upon Acute Blood Vessel Injury The Gax gene expression in normal blood vessels and in injured blood vessels was compared to determine whether Gax gene down-regulation occurs in response to injury-induced smooth muscle cell proliferation in vivo. Adult male Sprague-Dawley rats were subject to acute vessel injury by balloon de-endothelialization in the carotid arteries according to the methods of Majesky, M. W., et al. *J. Cell. Biol.* (1990) Vol. 111, pp. 2149–2158. The expression levels of Gax, that is, the mRNA levels, were assessed relative to that of glyceraldehyde 3-phosphate dehydrogenase (hereinafter also referred to as "G3") by a quantitative polymerase chain reaction. At various times following balloon de-endothelialization the rats were sacrificed and the total RNA was isolated from the vascular smooth muscle tissues using the TRI reagent from Molecular Research Center, Inc. The cDNA was synthesized from the extracted RNA with MMLV reverse transcriptase from Bethesda Research Labs. Aliquots of the cDNA pools were subjected to polymerase chain reaction amplification with AmpliTaq DNA polymerase from Perkin-Elmer in the presence of α32P-dCTP with the following cycle conditions: 94° C. for 20 seconds, 55° C. for 20 seconds, and 72° C. for 20 seconds. The final cycle had an elongation step at 72° C. for 5 minutes. The primers for the rat Gax amplification were: 5'-CCCGCGCGGCTTTTACATTAGGAGT-3' and 5'-GCTGGCAAACATGCCCTCCTCATTG-3'. The primers for the rat G3 gene were 5'-TGATGGCATGGACTGTGGTCATGA-3' and 5'-TGATGGCATGGACTGTGGTCATGA-3' SEQ ID NO: 16. The Gax cDNA was amplified for 30 cycles, and G3 was amplified for 25 cycles in the same reaction vessels. The amount of a radioactive label incorporated into the amplified cDNA and G3 fragments was determined by subjecting the fragments to electrophoresis on a 1% agarose gel, then excising the bands and liquid scintillation counting. Since the mRNA levels of glyceraldehyde 3-phosphate dehydrogenase remain relatively constant following this procedure (see J. M. Miano et al. 1990, *Am. J. Path.* 137, 761–765), the ratio of radiolabel incorporation into the Gax-derived amplified bands and the G3-derived amplified bands corrects for differences arising from the efficiency of RNA extraction from the different animals, and it provides a measure of Gax mRNA levels in the normal and injured vascular tissues. These ratios are plotted in FIG. 14.

Figure 14:
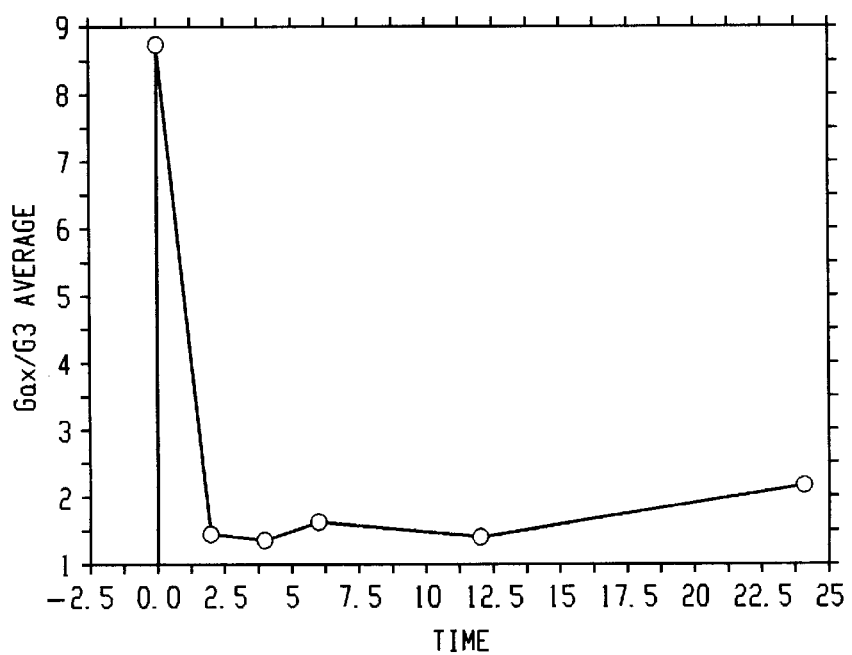
FIG. 14 is a graph showing the ratio of the Gax mRNA to glyceraldehyde-3-phosphate dehydrogenase designated "G3" level from normal vascular tissue and times following acute blood vessel injury.

As shown in FIG. 14, the Gax mRNA expression was down-regulated in response to acute vessel injury by as much as a factor of 20. This down-regulation was rapid and appeared complete by 2 hours, the first time-point following the de-endothelialization procedure. Collectively, these data corroborate the Gax gene down-regulation in cultures of vascular smooth muscle cells following growth factor stimulation. Further, these data show that Gax gene expression is an early marker of the cell cycle activity associated with the initiation of vascular restenosis, and they indicate that Gax has a regulatory role following blood vessel injury.

The present invention includes: the DNA sequences encoding a protein, or portion thereof, which inhibits vascular smooth muscle cell proliferation; the messenger RNA transcript of such DNA sequence; and an isolated protein which inhibits vascular smooth muscle cell growth.

For example, the DNA sequences include: DNA molecules which, but for the degeneracy of the genetic code would hybridize to DNA encoding the Gax protein, thus the degenerate DNA which encodes the Gax protein; DNA strands complementary to DNA sequences encoding the Gax protein or portions thereof including DNA in FIGS. 1 and 3 or portions thereof; heterologous DNA having substantial sequence homology to the DNA encoding the Gax protein, including the DNA sequences in FIGS. 1 and 3 or portions thereof.

The isolated protein includes, for example, portions of the Gax protein; the Gax protein of animals other than rat and human; and proteins or portions thereof having substantially the same amino acid sequence as shown in FIGS. 1 and 3 or portions thereof.

---

What is claimed is:

1. An isolated nucleic acid molecule comprising a nucleotide sequence encoding a human Gax protein, wherein said Gax protein is encoded by a Gax gene located on the short arm of human chromosome 7 and wherein said human Gax protein has a homeodomain, said homeodomain comprising amino acid 185 through amino acid 245 of the amino acid sequence set forth in SEQ. ID. NO. 4.

2. A vector comprising the nucleotide sequence of claim 1.

3. A host cell transformed by the vector of claim 2.

4. An isolated nucleic acid molecule comprising a nucleotide sequence encoding a human Gax protein that inhibits vascular smooth muscle cell proliferation, said human Gax protein having a molecular weight of from 30 to 36 kDa, and an amino acid sequence comprising: (a) a first region comprising amino acid 1 through amino acid 57 and amino acid 59 through amino acid 67 of SEQ. ID. NO. 4; (b) a second region of from about 11 to about 12 histidine residues; and (c) a third region comprising amino acid 76 through amino acid 87, amino acid 89 through amino acid 144, amino acid 146 through amino acid 156, amino acid 158 through amino acid 162, amino acid 164 through amino acid 287, amino acid 289 through amino acid 290, and amino acid 292 through amino acid 302 of SEQ. ID. NO. 4.

5. A vector comprising the nucleotide sequence of claim 4.

6. A host cell transformed by the vector of claim 5.

7. An isolated nucleic acid molecule encoding a human Gax protein that inhibits vascular smooth muscle cell proliferation, said nucleic acid molecule comprising a nucleotide sequence selected from the group consisting of:
- (a) nucleotide 699 through nucleotide 941 of the sequence set forth in SEQ. ID. NO. 3;
- (b) nucleotide 231 through nucleotide 698 of the sequence set forth in SEQ. ID. NO. 3;
- (c) nucleotide 119 through nucleotide 230 of the sequence set forth in SEQ. ID. NO. 3;
- (d) nucleotide 1 through nucleotide 118 of the sequence set forth in SEQ. ID. NO. 3;

and combinations thereof.

8. The isolated nucleic acid molecule of claim 7 wherein said Gax protein has a molecular weight of from about 30 kDa to about 36 kDa.

9. A vector comprising the nucleotide sequence of claim 7.

10. A host cell transformed by the vector of claim 9.

11. The nucleic acid of claim 7 wherein said nucleotide sequence comprises nucleotide 699 through nucleotide 941 of the sequence set forth in SEQ. ID.NO. 3.

12. The nucleic acid of claim 7 wherein said nucleotide sequence comprises nucleotide 231 through nucleotide 698 of the sequence set forth in SEQ.ID.NO. 3.

13. The nucleic acid of claim 7 wherein said nucleotide sequence comprises nucleotide 119 through nucleotide 230 of the sequence set forth in SEQ.ID.NO. 3.

14. The nucleic acid of claim 7 wherein said nucleotide sequence comprises nucleotide 1 through nucleotide 118 of the sequence set forth in SEQ.ID.NO. 3.

15. An isolated nucleic acid encoding a human Gax protein comprising an amino acid sequence selected from the group consisting of:
- (a) amino acid 223 through amino acid 302 of the sequence set forth in SEQ. ID. NO. 4;
- (b) amino acid 67 through amino acid 222 of the sequence set forth in SEQ. ID. NO. 4;
- (c) amino acid 30 through amino acid 66 of the sequence set forth in SEQ. ID. NO. 4;
- (d) amino acid 1 through amino acid 29 of the sequence set forth in SEQ. ID. NO. 4;

and combinations thereof.

16. A vector comprising the nucleotide sequence of claim 15.

17. A host cell transformed by the vector of claim 16.

18. The nucleic acid of claim 15 wherein said nucleic acid encodes amino acid 223 through amino acid 302 of the sequence set forth in SEQ.ID.NO. 4.

19. The nucleic acid of claim 15 wherein said nucleic acid encodes amino acid 67 through amino acid 222 of the sequence set forth in SEQ.ID.NO. 4.

20. The nucleic acid of claim 15 wherein said nucleic acid encodes amino acid 30 through amino acid 66 of the sequence set forth in SEQ.ID.NO. 4.

* * * * *

UNITED STATES PATENT AND TRADEMARK OFFICE
CERTIFICATE OF CORRECTION

PATENT NO.       : 6,280,969 B1                                      Page 1 of 1
APPLICATION NO.  : 09/078465
DATED            : August 28, 2001
INVENTOR(S)      : David H. Gorski and Kenneth Walsh It is certified that error appears in the above-identified patent and that said Letters Patent is hereby corrected as shown below:

Column 1, before BACKGROUND OF THE INVENTION, please insert -- This invention was made with government support under grant number HL45345 awarded by the National Institutes of Health. The government has certain rights in the invention. --

Signed and Sealed this

Twenty-first Day of August, 2007

JON W. DUDAS
*Director of the United States Patent and Trademark Office*

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 2244 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 197..1108

(xi) SEQUENCE DESCRIPTION: SEQ ID NO:1:

```
GTCAAGTGTT TATACGTGCA GGAGACTGGC CGCTCGGCTC AGGACTGGGA TTAGCGGGCT      60

CTGCTCAAAC CCGCGCGGCT TTTACATTAG GAGTGAGTGG GGGAGAGTCC TAGGATTTCT     120

AGTGAAAAGT GACAGCGCTT GGTGGACTTT GGGACCTTCG TGAAGTCTTC TGCTTGGAAG     180

CTGAGACTTG CATGCC ATG GAA CAC CCC CTC TTT GGC TGC CTG CGC AGC         229
                Met Glu His Pro Leu Phe Gly Cys Leu Arg Ser
                 1               5                   10

CCC CAC GCC ACA GCG CAA GGC TTG CAC CCC TTC TCG CAG TCT TCT CTG       277
Pro His Ala Thr Ala Gln Gly Leu His Pro Phe Ser Gln Ser Ser Leu
            15                  20                  25

GCC CTC CAT GGA AGA TCT GAC CAC ATG TCC TAC CCC GAA CTC TCC ACA       325
Ala Leu His Gly Arg Ser Asp His Met Ser Tyr Pro Glu Leu Ser Thr
        30                  35                  40

TCT TCC TCG TCT TGC ATA ATC GCG GGA TAC CCC AAT GAG GAG GGC ATG       373
Ser Ser Ser Ser Cys Ile Ile Ala Gly Tyr Pro Asn Glu Glu Gly Met
    45                  50                  55

TTT GCC AGC CAG CAT CAC AGG GGG CAC CAC CAC CAC CAC CAC CAC CAC       421
Phe Ala Ser Gln His His Arg Gly His His His His His His His His
60                  65                  70                  75

CAT CAC CAC CAC CAG CAG CAG CAG CAC CAG GCT CTG CAA AGC AAC TGG       469
His His His His Gln Gln Gln Gln His Gln Ala Leu Gln Ser Asn Trp
                80                  85                  90

CAC CTC CCG CAG ATG TCC TCC CCG CCA AGC GCG GCC CGG CAC AGC CTT       517
His Leu Pro Gln Met Ser Ser Pro Pro Ser Ala Ala Arg His Ser Leu
            95                  100                 105

TGC CTG CAG CCT GAT TCC GGA GGG CCC CCG GAG CTG GGG AGC AGC CCT       565
Cys Leu Gln Pro Asp Ser Gly Gly Pro Pro Glu Leu Gly Ser Ser Pro
        110                 115                 120

CCG GTC CTG TGC TCC AAC TCT TCT AGC CTG GGC TCC AGC ACC CCG ACC       613
Pro Val Leu Cys Ser Asn Ser Ser Ser Leu Gly Ser Ser Thr Pro Thr
    125                 130                 135

GGA GCC GCG TGC GCA CCA AGG GAT TAT GGC CGT CAA GCG CTG TCA CCC       661
Gly Ala Ala Cys Ala Pro Arg Asp Tyr Gly Arg Gln Ala Leu Ser Pro
```

```
140                 145                 150                 155
GCA GAA GTG GAG AAG AGA AGT GGC AGC AAA AGA AAA AGC GAC AGT TCA         709
Ala Glu Val Glu Lys Arg Ser Gly Ser Lys Arg Lys Ser Asp Ser Ser
                    160                 165                 170

GAT TCC CAG GAA GGA AAT TAC AAG TCA GAA GTG AAC AGC AAA CCT AGG         757
Asp Ser Gln Glu Gly Asn Tyr Lys Ser Glu Val Asn Ser Lys Pro Arg
            175                 180                 185

AGG GAA AGA ACA GCT TTC ACC AAA GAG CAA ATC AGA GAA CTT GAG GCA         805
Arg Glu Arg Thr Ala Phe Thr Lys Glu Gln Ile Arg Glu Leu Glu Ala
            190                 195                 200

GAG TTC GCC CAT CAT AAC TAT CTG ACC AGA CTG AGA AGA TAT GAG ATA         853
Glu Phe Ala His His Asn Tyr Leu Thr Arg Leu Arg Arg Tyr Glu Ile
        205                 210                 215

GCG GTG AAC CTA GAC CTC ACT GAA AGA CAG GTG AAA GTG TGG TTC CAG         901
Ala Val Asn Leu Asp Leu Thr Glu Arg Gln Val Lys Val Trp Phe Gln
220                 225                 230                 235

AAC AGG AGA ATG AAG TGG AAG CGG GTC AAG GGG GGA CAA CAA GGA GCT         949
Asn Arg Arg Met Lys Trp Lys Arg Val Lys Gly Gly Gln Gln Gly Ala
                240                 245                 250

GCA GCC CGA GAA AAG GAA CTG GTG AAT GTG AAA AAG GGA ACA CTT CTT         997
Ala Ala Arg Glu Lys Glu Leu Val Asn Val Lys Lys Gly Thr Leu Leu
            255                 260                 265

CCA TCA GAG CTG TCA GGA ATT GGT GCA GCC ACC CTC CAG CAG ACA GGG        1045
Pro Ser Glu Leu Ser Gly Ile Gly Ala Ala Thr Leu Gln Gln Thr Gly
        270                 275                 280

GAC TCA CTA GCA AAT GAC GAC AGT CGC GAT AGT GAC CAC AGC TCT GAG        1093
Asp Ser Leu Ala Asn Asp Asp Ser Arg Asp Ser Asp His Ser Ser Glu
    285                 290                 295

CAC GCA CAC TTA TGATACATAC AGAGACCAGC TCCGTTCTCA GGAAAGCACC            1145
His Ala His Leu
300

ATTGTGATGG CAAATCTCAC CCAAACATCG TTTACATGGC AGATGACTGT GGCAGTGTTG      1205

CTTAATATAA TTAAACGCAG GCATCTCAAG TCTGTTTCTC ATGATTGATA AAGGTTTAC       1265

ACTAAGTGCC TCTTATTGAA GATGCTTCCA CAGTGAAATT GGAGAAAGTG AACATATCTA      1325

AATATACTTG TTCCTTATAT GACAGAGAGG GAGATGAATG TTTGCTTTGG CTTGCACTGA      1385

AAATTAAATT GCTACCAAGA GCAAACTCGG TAAGACATTT TGACTCAAGT TGTCTCCAGA      1445

GTGAAGATGT TATAGAAATG CTTTGAACAT TCCAGTTGTA CCAGGTCATG TGTGTGACAC      1505

TGGGCAGGTA TTTGCTTTTG CTTGCACTGA AACTTAAACT GCTATCAAGT TAACCCATGA      1565

AATAGTTTAT CTTGAACAGC CACAGTGCCT GAAATCACCA AGTGGATATA AAATGAACTG      1625

AAATTCTGTA TATATTACTC CTAAGTCATT TTCCTGTCTT CACTAATTTT AGCAAATGCA      1685

TTCATATTAG CTGATGAAAA TAGGCTTTCC CGTGGACAAA TGCAGCCAGC TTCTTGTATT      1745

TTTATACATT TTTTTGTCAG TCAGAGACAT CAGTATGTGC TTACTTGTGT TCAAGTAGAG      1805

GAAATGCAGT AGAGTCTGAT AGGACATATT CTTGGTACCA CAGACAAAAC AAATCTTCTG      1865

TTGCATTGAC TATCAACTGC TGCAGATACA TTAGAGAACA CACCTAGCCC CCTCCAGCC      1925

TCCCTCTGTT ATCGCTCGAA GACATTAGCG TCATAGGCAA GTAGTTACCT TGCCAAATGA      1985

GTCTTGTGTG GCAGATGTCT GATTTTGTAT CTTTAAACTG TTAATGGTAT GTGTCTGCTT      2045

CAGTTAACAG GGAAAAAGAT TCTTCCTCA TTGTTTATGA TACAAAACCC AAGTGCCAAA       2105

CAAAGCTAGT TCTTCAAGGG ATAGATGAGA AACTGAATGT CTGACAAGTA GACTCAGCGA      2165

AAATACATTA TTTTTCAGAG GCTGTGTATT CATGCAGTAC AAGTCCTTGT ATTTTGTAAA      2225

AAAAAAGTT AAATAAATG                                                    2244
```

(2) INFORMATION FOR SEQ ID NO:2:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu His Pro Leu Phe Gly Cys Leu Arg Ser Pro His Ala Thr Ala
 1               5                  10                  15

Gln Gly Leu His Pro Phe Ser Gln Ser Ser Leu Ala Leu His Gly Arg
             20                  25                  30

Ser Asp His Met Ser Tyr Pro Glu Leu Ser Thr Ser Ser Ser Ser Cys
         35                  40                  45

Ile Ile Ala Gly Tyr Pro Asn Glu Glu Gly Met Phe Ala Ser Gln His
     50                  55                  60

His Arg Gly His His His His His His His His His His His Gln
 65                  70                  75                  80

Gln Gln Gln His Gln Ala Leu Gln Ser Asn Trp His Leu Pro Gln Met
             85                  90                  95

Ser Ser Pro Pro Ser Ala Ala Arg His Ser Leu Cys Leu Gln Pro Asp
            100                 105                 110

Ser Gly Gly Pro Pro Glu Leu Gly Ser Ser Pro Val Leu Cys Ser
            115                 120                 125

Asn Ser Ser Ser Leu Gly Ser Ser Thr Pro Thr Gly Ala Ala Cys Ala
130                 135                 140

Pro Arg Asp Tyr Gly Arg Gln Ala Leu Ser Pro Ala Glu Val Glu Lys
145                 150                 155                 160

Arg Ser Gly Ser Lys Arg Lys Ser Asp Ser Asp Ser Gln Glu Gly
                165                 170                 175

Asn Tyr Lys Ser Glu Val Asn Ser Lys Pro Arg Arg Glu Arg Thr Ala
                180                 185                 190

Phe Thr Lys Glu Gln Ile Arg Glu Leu Glu Ala Glu Phe Ala His His
            195                 200                 205

Asn Tyr Leu Thr Arg Leu Arg Arg Tyr Glu Ile Ala Val Asn Leu Asp
210                 215                 220

Leu Thr Glu Arg Gln Val Lys Val Trp Phe Gln Asn Arg Arg Met Lys
225                 230                 235                 240

Trp Lys Arg Val Lys Gly Gly Gln Gln Gly Ala Ala Ala Arg Glu Lys
                245                 250                 255

Glu Leu Val Asn Val Lys Lys Gly Thr Leu Leu Pro Ser Glu Leu Ser
                260                 265                 270

Gly Ile Gly Ala Ala Thr Leu Gln Gln Thr Gly Asp Ser Leu Ala Asn
            275                 280                 285

Asp Asp Ser Arg Asp Ser Asp His Ser Ser Glu His Ala His Leu
            290                 295                 300
```

(2) INFORMATION FOR SEQ ID NO:3:

(i) SEQUENCE CHARACTERISTICS:
        (A) LENGTH: 941 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 33..941

(xi) SEQUENCE DESCRIPTION: SEQ ID NO:3:

```
GTCTTCTACC TGGAACCCGA AACTTGCATG CT ATG GAA CAC CCG CTC TTT GGC         53
                                   Met Glu His Pro Leu Phe Gly
                                    1               5

TGC CTG CGC AGC CCT CAC GCC ACG GCG CAA GGC TTG CAC CCG TTC TCC        101
Cys Leu Arg Ser Pro His Ala Thr Ala Gln Gly Leu His Pro Phe Ser
         10                  15                  20

CAA TCC TCT CTC GCC CTC CAT GGA AGA TCT GAC CAT ATG TCT TAC CCC        149
Gln Ser Ser Leu Ala Leu His Gly Arg Ser Asp His Met Ser Tyr Pro
     25                  30                  35

GAG CTC TCT ACT TCT TCC TCA TCT TGC ATA ATC GCG GGA TAC CCC AAC        197
Glu Leu Ser Thr Ser Ser Ser Ser Cys Ile Ile Ala Gly Tyr Pro Asn
 40                  45                  50                  55

GAA GAG GAC ATG TTT GCC AGC CAG CAT CAC AGG GGG CAC CAC CAC CAC        245
Glu Glu Asp Met Phe Ala Ser Gln His His Arg Gly His His His His
                 60                  65                  70

CAC CAC CAC CAT CAC CAC CAT CAG CAG CAG CAG CAC CAG GCT CTG CAA        293
His His His His His His His Gln Gln Gln Gln His Gln Ala Leu Gln
             75                  80                  85

ACC AAC TGG CAC CTC CCG CAG ATG TCT TCC CCA CCG AGT GCG GCT CGG        341
Thr Asn Trp His Leu Pro Gln Met Ser Ser Pro Pro Ser Ala Ala Arg
         90                  95                 100

CAT AGC CTC TGC CTC CAG CCC GAC TCT GGA GGG CCC CCA GAG TTG GGG        389
His Ser Leu Cys Leu Gln Pro Asp Ser Gly Gly Pro Pro Glu Leu Gly
    105                 110                 115

AGC AGC CCG CCC GTC CTG TGC TCC AAC TCT TCC AGC TTG GGC TCC AGC        437
Ser Ser Pro Pro Val Leu Cys Ser Asn Ser Ser Ser Leu Gly Ser Ser
120                 125                 130                 135

ACC CCG ACT GGG GCC GCG TGC GCG CCG GGG GAC TAC GGC CGC CAG GCA        485
Thr Pro Thr Gly Ala Ala Cys Ala Pro Gly Asp Tyr Gly Arg Gln Ala
                140                 145                 150

CTG TCA CCT GCG GAG GCG GAG AAG CGA AGC GGC GGC AAG AGG AAA AGC        533
Leu Ser Pro Ala Glu Ala Glu Lys Arg Ser Gly Gly Lys Arg Lys Ser
            155                 160                 165

GAC AGC TCA GAC TCC CAG GAA GGA AAT TAC AAG TCA GAA GTC AAC AGC        581
Asp Ser Ser Asp Ser Gln Glu Gly Asn Tyr Lys Ser Glu Val Asn Ser
        170                 175                 180

AAA CCC AGG AAA GAA AGG ACA GCA TTT ACC AAA GAG CAA ATC AGA GAA        629
Lys Pro Arg Lys Glu Arg Thr Ala Phe Thr Lys Glu Gln Ile Arg Glu
    185                 190                 195

CTT GAA GCA GAA TTT GCC CAT CAT AAT TAT CTC ACC AGA CTG AGG CGA        677
Leu Glu Ala Glu Phe Ala His His Asn Tyr Leu Thr Arg Leu Arg Arg
200                 205                 210                 215

TAC GAG ATA GCA GTG AAT CTG GAT CTC ACT GAA AGA CAG GTA AAA GTC        725
Tyr Glu Ile Ala Val Asn Leu Asp Leu Thr Glu Arg Gln Val Lys Val
                220                 225                 230

TGG TTC CAA AAC AGG CGG ATG AAG TGG AAG AGG GTA AAG GGT GGA CAG        773
Trp Phe Gln Asn Arg Arg Met Lys Trp Lys Arg Val Lys Gly Gly Gln
            235                 240                 245

CAA GGA GCT GCG GCT CGG GAA AAG GAA CTG GTG AAT GTG AAA AAG GGA        821
Gln Gly Ala Ala Ala Arg Glu Lys Glu Leu Val Asn Val Lys Lys Gly
        250                 255                 260
```

```
ACA CTT CTC CCA TCA GAG CTG TCG GGA ATT GGT GCA GCC ACC CTC CAG        869
Thr Leu Leu Pro Ser Glu Leu Ser Gly Ile Gly Ala Ala Thr Leu Gln
    265                 270                 275

CAA ACA GGG GAC TCT ATA GCA AAT GAA GAC AGT CAC GAC AGT GAC CAC        917
Gln Thr Gly Asp Ser Ile Ala Asn Glu Asp Ser His Asp Ser Asp His
280                 285                 290                 295

AGC TCA GAG CAC GCC CAC CTC TGA                                        941
Ser Ser Glu His Ala His Leu
            300
```

(2) INFORMATION FOR SEQ ID NO:4:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu His Pro Leu Phe Gly Cys Leu Arg Ser Pro His Ala Thr Ala
 1               5                  10                  15

Gln Gly Leu His Pro Phe Ser Gln Ser Ser Leu Ala Leu His Gly Arg
                20                  25                  30

Ser Asp His Met Ser Tyr Pro Glu Leu Ser Thr Ser Ser Ser Ser Cys
            35                  40                  45

Ile Ile Ala Gly Tyr Pro Asn Glu Glu Asp Met Phe Ala Ser Gln His
        50                  55                  60

His Arg Gly His His His His His His His His His Gln Gln
 65                 70                  75                  80

Gln Gln His Gln Ala Leu Gln Thr Asn Trp His Leu Pro Gln Met Ser
                85                  90                  95

Ser Pro Pro Ser Ala Ala Arg His Ser Leu Cys Leu Gln Pro Asp Ser
            100                 105                 110

Gly Gly Pro Pro Glu Leu Gly Ser Ser Pro Val Leu Cys Ser Asn
        115                 120                 125

Ser Ser Ser Leu Gly Ser Ser Thr Pro Thr Gly Ala Ala Cys Ala Pro
130                 135                 140

Gly Asp Tyr Gly Arg Gln Ala Leu Ser Pro Ala Glu Ala Glu Lys Arg
145                 150                 155                 160

Ser Gly Gly Lys Arg Lys Ser Asp Ser Ser Asp Ser Gln Glu Gly Asn
                165                 170                 175

Tyr Lys Ser Glu Val Asn Ser Lys Pro Arg Lys Glu Arg Thr Ala Phe
            180                 185                 190

Thr Lys Glu Gln Ile Arg Glu Leu Glu Ala Glu Phe Ala His His Asn
        195                 200                 205

Tyr Leu Thr Arg Leu Arg Arg Tyr Glu Ile Ala Val Asn Leu Asp Leu
    210                 215                 220

Thr Glu Arg Gln Val Lys Val Trp Phe Gln Asn Arg Arg Met Lys Trp
225                 230                 235                 240

Lys Arg Val Lys Gly Gly Gln Gln Gly Ala Ala Ala Arg Glu Lys Glu
                245                 250                 255

Leu Val Asn Val Lys Lys Gly Thr Leu Leu Pro Ser Glu Leu Ser Gly
            260                 265                 270

Ile Gly Ala Ala Thr Leu Gln Gln Thr Gly Asp Ser Ile Ala Asn Glu
        275                 280                 285
```

```
Asp Ser His Asp Ser Asp His Ser Ser Glu His Ala His Leu
    290                 295                 300
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 21
        (D) OTHER INFORMATION: /mod_base= i (ix) FEATURE:
        (A) NAME/KEY: modified_base
        (B) LOCATION: 24
        (D) OTHER INFORMATION: /mod_base= i (xi) SEQUENCE DESCRIPTION: SEQ ID NO:5:

AARATWTGGT TYCARAAYMG WMGWATGAA                                    29

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (ix) FEATURE:
        (A) NAME/KEY: modified_base
        (B) LOCATION: 4
        (D) OTHER INFORMATION: /mod_base= i (xi) SEQUENCE DESCRIPTION: SEQ ID NO:6:

TCAWARRTGW GCRTGYTC                                                  18

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

GCGCGCAGAT CTCACTGAAA GACAGGTAAA                                  30

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

TTTACCTGTC TTTCAGTGAG                                20

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

GCGCGCAGAT CTAGATTCAC TGCTATCTCG TA                  32

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:10:

GCGCGTGCCC CCTCTGATGC TGGCTGGCAA ACATGT              36

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:11:

GCGCGCTCTT GAAGGGCGAG AGAGGATTGG GA                  32

(2) INFORMATION FOR SEQ ID NO:12:

(i) SEQUENCE CHARACTERISTICS:

(A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

CTGGTTCGGC CCACCTCTGA AGGTTCCAGA ATCGATAG                                38

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

GGAGACTTCC AAGGTCTTAG CTATCACTTA AGCAC                                   35

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:14:

GCGCGCGTCG ACGAACACCC CCTCTTTGGC                                         30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

GCGCGCAAGC TTTCATAAGT GTGCGTGCTC                                         30

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear -continued (ii) MOLECULE TYPE: cDNA (iii) HYPOTHETICAL: NO (iv) ANTI-SENSE: NO (xi) SEQUENCE DESCRIPTION: SEQ ID NO:16:

CCCGCGCGGC TTTTACATTA GGAGT                                          25

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

GCTGGCAAAC ATGCCCTCCT CATTG                                          25

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

TGATGGCATG GACTGTGGTC ATGA                                           24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

TGATGGCATG GACTGTGGTC ATGA                                           24